United States Patent

Lesh et al.

[11] Patent Number: 6,024,740
[45] Date of Patent: Feb. 15, 2000

[54] CIRCUMFERENTIAL ABLATION DEVICE ASSEMBLY

[75] Inventors: Michael D. Lesh, Mill Valley; Michael Ronald Ross, Hillsborough, both of Calif.; Jonathan J. Langberg, Atlanta, Ga.; James C. Peacock, III, Sunnyvale, Calif.

[73] Assignees: The Regents of the University of California, Oakland; Atrionix, Inc., Palo Alto, both of Calif.; Emory University, Atlanta, Ga.

[21] Appl. No.: 08/889,798

[22] Filed: Jul. 8, 1997

[51] Int. Cl.$^7$ ................................................. A61B 17/38
[52] U.S. Cl. .............................................................. 606/34
[58] Field of Search ................................... 600/373, 374, 600/375, 381; 606/32, 40, 41, 46, 47, 48, 34; 607/122; 601/2

[56] References Cited

U.S. PATENT DOCUMENTS

| Re. 35,880 | 8/1998 | Waldman et al. . |
|---|---|---|
| 4,441,266 | 4/1984 | Cosman . |
| 4,449,528 | 5/1984 | Auth et al. . |
| 4,522,205 | 6/1985 | Taylor et al. . |
| 4,569,801 | 2/1986 | Molloy et al. . |

(List continued on next page.)

FOREIGN PATENT DOCUMENTS

| WO 93/00958 | 1/1993 | WIPO . |
|---|---|---|
| WO 93/08755 | 5/1993 | WIPO . |
| WO 93/16632 | 9/1993 | WIPO . |
| WO 93/20767 | 10/1993 | WIPO . |
| WO 93/20886 | 10/1993 | WIPO . |

(List continued on next page.)

OTHER PUBLICATIONS

Jais et al., "Biatrial Dimensions Relevant to Catheter Ablation" North American Society of Pacing and Electrophysiology, 17th Annual Scientific Sessions Abstract Form.

Jais et al., "A focal source of atrial fibrillation treated by discete radiofrequency ablation" Circulation (1997)95:572–576.

Avitall, et al., "Physics and Engineering of Transcatheter Tissue Ablation" *J. of Am. College of Card.* 22(3):921–932 (1993).

(List continued on next page.)

*Primary Examiner*—George Manuel
*Attorney, Agent, or Firm*—Knobbe, Martens, Olson & Bear, LLP

[57] ABSTRACT

This invention is a circumferential ablation device assembly which is adapted to forming a circumferential conduction block in a pulmonary vein. The assembly includes a circumferential ablation element which is adapted to ablate a circumferential region of tissue along a pulmonary vein wall which circumscribes the pulmonary vein lumen, thereby transecting the electrical conductivity of the pulmonary vein against conduction along its longitudinal axis and into the left atrium. The circumferential ablation element includes an expandable member with a working length that is adjustable from a radially collapsed position to a radially expanded position. An equatorial band circumscribes the outer surface of the working length and is adapted to ablate tissue adjacent thereto when actuated by an ablation actuator. The equatorial band has a length relative to the longitudinal axis of the expandable member that is narrow relative to the working length, and is also substantially shorter than its circumference when the working length is in the radially expanded position. A pattern of insulators may be included over an ablation element which otherwise spans the working length in order to form the equatorial band described. The expandable member is also adapted to conform to the pulmonary vein in the region of its ostium, such as by providing a great deal of radial compliance or by providing a taper along the working length which has a distally reducing outer diameter. A linear ablation element is provided adjacent to the circumferential ablation element in a combination assembly which is adapted for use in a less-invasive "maze"-type procedure in the region of the pulmonary vein ostia in the left ventricle.

81 Claims, 17 Drawing Sheets

U.S. PATENT DOCUMENTS

| | | |
|---|---|---|
| 4,641,649 | 2/1987 | Walinsky et al. . |
| 4,660,571 | 4/1987 | Hess et al. . |
| 4,662,368 | 5/1987 | Hussein et al. . |
| 4,672,962 | 6/1987 | Hershenson . |
| 4,673,563 | 6/1987 | Berne et al. . |
| 4,676,258 | 6/1987 | Inokuchi et al. . |
| 4,790,311 | 12/1988 | Ruiz . |
| 4,807,620 | 2/1989 | Strul et al. . |
| 4,898,591 | 2/1990 | Jang et al. . |
| 4,924,863 | 5/1990 | Sterzer . |
| 4,940,064 | 7/1990 | Desai . |
| 4,945,912 | 8/1990 | Langberg . |
| 4,976,711 | 12/1990 | Parins et al. .............................. 606/48 |
| 4,998,933 | 3/1991 | Eggers et al. . |
| 5,035,694 | 7/1991 | Kasprzyk et al. . |
| 5,078,717 | 1/1992 | Parins et al. . |
| 5,078,736 | 1/1992 | Behl . |
| 5,104,393 | 4/1992 | Isner et al. . |
| 5,147,355 | 9/1992 | Friedman et al. . |
| 5,178,618 | 1/1993 | Kandarpa . |
| 5,190,540 | 3/1993 | Lee . |
| 5,226,430 | 7/1993 | Spears et al. . |
| 5,228,442 | 7/1993 | Imran . |
| 5,231,995 | 8/1993 | Desai . |
| 5,255,679 | 10/1993 | Imran . |
| 5,263,493 | 11/1993 | Avitall . |
| 5,292,321 | 3/1994 | Lee . |
| 5,293,868 | 3/1994 | Nardella . |
| 5,293,869 | 3/1994 | Edwards et al. . |
| 5,295,484 | 3/1994 | Marcus et al. . |
| 5,313,943 | 5/1994 | Houser et al. . |
| 5,324,255 | 6/1994 | Passafaro et al. . |
| 5,324,284 | 6/1994 | Imram ...................................... 606/15 |
| 5,342,292 | 8/1994 | Nita et al. . |
| 5,344,435 | 9/1994 | Turner et al. . |
| 5,345,936 | 9/1994 | Pomeranz et al. . |
| 5,348,554 | 9/1994 | Imran et al. . |
| 5,368,558 | 11/1994 | Nita . |
| 5,370,678 | 12/1994 | Edwards et al. . |
| 5,385,544 | 1/1995 | Edwards et al. . |
| 5,391,197 | 2/1995 | Burdette et al. . |
| 5,423,808 | 6/1995 | Edwards et al. . |
| 5,423,811 | 6/1995 | Imran et al. . |
| 5,427,119 | 6/1995 | Swartz et al. . |
| 5,433,708 | 7/1995 | Nichols et al. . |
| 5,447,509 | 9/1995 | Mills et al. . |
| 5,449,380 | 9/1995 | Chin . |
| 5,456,682 | 10/1995 | Edwards et al. . |
| 5,474,530 | 12/1995 | Passafaro et al. . |
| 5,484,400 | 1/1996 | Edwards et al. . |
| 5,487,385 | 1/1996 | Avitall . |
| 5,497,119 | 3/1996 | Tedrow . |
| 5,497,774 | 3/1996 | Swartz et al. . |
| 5,505,702 | 4/1996 | Arney . |
| 5,505,730 | 4/1996 | Edwards . |
| 5,522,873 | 6/1996 | Jackman et al. . |
| 5,545,161 | 8/1996 | Imran . |
| 5,545,193 | 8/1996 | Fleischman et al. . |
| 5,549,661 | 8/1996 | Kordis et al. . |
| 5,558,720 | 9/1996 | Sarraf et al. . |
| 5,562,720 | 10/1996 | Stern et al. . |
| 5,564,440 | 10/1996 | Swartz et al. . |
| 5,571,088 | 11/1996 | Lennox et al. . |
| 5,575,766 | 11/1996 | Swartz et al. . |
| 5,575,772 | 11/1996 | Lennox . |
| 5,575,788 | 11/1996 | Baker et al. . |
| 5,575,810 | 11/1996 | Munsif . |
| 5,582,609 | 12/1996 | Swanson et al. . |
| 5,588,432 | 12/1996 | Crowley . |
| 5,606,974 | 3/1997 | Castellano et al. . |
| 5,607,422 | 3/1997 | Smeets et al. . |
| 5,617,854 | 4/1997 | Munsif . |
| 5,620,479 | 4/1997 | Diederich . |
| 5,630,837 | 5/1997 | Crowley ...................................... 601/2 |
| 5,642,736 | 7/1997 | Avitall . |
| 5,645,082 | 7/1997 | Sung et al. . |
| 5,658,278 | 8/1997 | Imran et al. . |
| 5,673,695 | 10/1997 | McGee et al. . |
| 5,676,662 | 10/1997 | Fleischhacker et al. . |
| 5,683,445 | 11/1997 | Swoyer . |
| 5,685,322 | 11/1997 | Sung et al. . |
| 5,685,839 | 11/1997 | Edwards et al. . |
| 5,687,723 | 11/1997 | Aviall . |
| 5,687,729 | 11/1997 | Schaetzle . |
| 5,688,267 | 11/1997 | Panescu et al. . |
| 5,690,611 | 11/1997 | Swartz et al. . |
| 5,693,078 | 12/1997 | Desai et al. . |
| 5,697,925 | 12/1997 | Taylor . |
| 5,697,927 | 12/1997 | Imran et al. . |
| 5,702,438 | 12/1997 | Avitall . |
| 5,715,818 | 2/1998 | Swartz et al. . |
| 5,716,389 | 2/1998 | Walinsky et al. . |
| 5,718,231 | 2/1998 | Dewhurst et al. . |
| 5,718,241 | 2/1998 | Ben-Haim et al. . |
| 5,718,701 | 2/1998 | Shai et al. . |
| 5,720,775 | 2/1998 | Larnard . |
| 5,722,401 | 3/1998 | Pietroski et al. ........................ 600/374 |
| 5,722,403 | 3/1998 | McGee et al. ........................... 128/642 |
| 5,722,963 | 3/1998 | Lurie et al. . |
| 5,725,512 | 3/1998 | Swartz et al. . |
| 5,730,127 | 3/1998 | Avitall . |
| 5,730,704 | 3/1998 | Avitall . |
| 5,733,315 | 3/1998 | Burdette et al. . |
| 5,735,280 | 4/1998 | Sherman et al. . |
| 5,735,846 | 4/1998 | Panescu et al. . |
| 5,741,249 | 4/1998 | Moss et al. . |
| 5,741,320 | 4/1998 | Thornton et al. . |
| 5,743,870 | 4/1998 | Edwards . |
| 5,743,903 | 4/1998 | Stern et al. . |
| 5,755,663 | 5/1998 | Larsen et al. . |
| 5,755,664 | 5/1998 | Rubenstein . |
| 5,755,715 | 5/1998 | Stern et al. . |
| 5,755,760 | 5/1998 | Maguire et al. . |
| 5,769,846 | 6/1998 | Edwards et al. . |
| 5,782,239 | 7/1998 | Webster, Jr. . |
| 5,797,877 | 8/1998 | Hamilton et al. . |
| 5,797,903 | 8/1998 | Swanson et al. ........................ 606/34 |
| 5,797,905 | 8/1998 | Fleischman et al. . |
| 5,800,378 | 9/1998 | Edwards et al. . |
| 5,800,379 | 9/1998 | Edwards . |
| 5,800,413 | 9/1998 | Swartz et al. . |
| 5,800,428 | 9/1998 | Nelson et al. . |
| 5,800,429 | 9/1998 | Edwards . |
| 5,807,249 | 9/1998 | Qin et al. . |
| 5,807,308 | 9/1998 | Edwards . |
| 5,807,391 | 9/1998 | Wijkamp . |
| 5,807,395 | 9/1998 | Mulier et al. . |

FOREIGN PATENT DOCUMENTS

| | | |
|---|---|---|
| WO 94/00050 | 1/1994 | WIPO . |
| WO 94/21165 | 9/1994 | WIPO . |
| WO 94/21167 | 9/1994 | WIPO . |
| WO 94/21168 | 9/1994 | WIPO . |
| WO 95/10318 | 4/1995 | WIPO . |
| WO 95/10319 | 4/1995 | WIPO . |
| WO 95/10321 | 4/1995 | WIPO . |
| WO 96/00036 | 1/1996 | WIPO . |
| WO 96/10961 | 4/1996 | WIPO . |
| WO 96/26675 | 9/1996 | WIPO . |
| WO 96/32885 | 10/1996 | WIPO . |
| WO 96/32897 | 10/1996 | WIPO . |
| WO 97/32525 | 9/1997 | WIPO . |

| WO 97/37607 | 10/1997 | WIPO . |
| WO 97/45156 | 12/1997 | WIPO . |
| WO 98/02201 | 1/1998 | WIPO . |

OTHER PUBLICATIONS

Cox, JL "The Surgical Treatment of Atrial Fibrillation-.I.Summary" *Thoracic and Cardiovascular Surgery* 101(4):584–592 (1991).

Cox, JL et al., "The Surgical Treatment of Atrial Fibrillation.I.Summary" *Thoracic and Cardiovascular Surgery* 101(3):402–405 (1991).

Fram, et al., "Feasibility of RF Powered Thermal Balloon Ablation of Atrioventricular Bypass Tracts via the Coronary Sinus: In Vivo Canine Studies" *PACE* 18:1518–1530 (1995).

Haissaguerre, et al., "Right and Left Atrial Radiofrequency Catheter Therapy of Paroxysmal Atrial Fibrillation" *J. of Cardiovascular Electrophysiology* 7(12):1132–1144 (1996).

Hindricks, et al., "IX Nonpharmacologic Management" *Current Management of Arrhythmias* pp. 373–378 (1991).

Jais, et al., "A Focal Source of Atrial Fibrillation Treated by Discrete Radiofrequency Ablation" *Circulation* 95:572–576 (1997).

McMath, LP et al., "Percutaneous Laser Balloon Coagulation of Accessory Pathways" *Diagn Ther Cardiovasc Interven* 1425:165–171 (1991).

Schuger, CD et al., "Long–Term Effects of Percutaneous Laser Balloon Ablation from the Canine Coronary Sinus" *Circulation* 86:947–954 (1992).

Sueda, et al., "Simple Left Atrial Procedure for Chronic Atrial Fibrillation Associated With Mitral Valve Disease" *Ann Thorac Surg* 62:1796–1800 (1996).

CIRCUMFERENTIAL ABLATION DEVICE ASSEMBLY

TECHNICAL FIELD

The present invention is a surgical device. More specifically, it is a circumferential ablation device assembly which is adapted to ablate a selected circumferential region of tissue along a pulmonary vein wall and thereby form a circumferential conduction block against conduction along the longitudinal axis of the pulmonary vein wall.

BACKGROUND

Many abnormal medical conditions in humans and other mammals have been associated with disease and other aberrations along the lining or walls which define several different body spaces. In order to treat such abnormal wall conditions of the body spaces, medical device technologies adapted for delivering specific forms of ablative energy to specific regions of targeted wall tissue from within the associated body space have been developed and disclosed.

The terms "body space," including derivatives thereof, is herein intended to mean any cavity or lumen within the body which is defined at least in part by a tissue wall. For example, the cardiac chambers, the uterus, the regions of the gastrointestinal tract, and the arterial or venous vessels are all considered illustrative examples of body spaces within the intended meaning.

The term "lumen," including derivatives thereof, is herein intended to mean any body space which is circumscribed along a length by a tubular tissue wall and which terminates at each of two ends in at least one opening that communicates externally of the body space. For example, the large and small intestines, the vas deferens, the trachea, and the fallopian tubes are all illustrative examples of lumens within the intended meaning. Blood vessels are also herein considered lumens, including regions of the vascular tree between their branch points. More particularly, the pulmonary veins are lumens within the intended meaning, including the region of the pulmonary veins between the branched portions of their ostia along a left ventricle wall, although the wall tissue defining the ostia typically presents uniquely tapered lumenal shapes.

Atherosclerosis, a vascular disease characterized by abnormal deposits upon vessel walls or thickening thereof, is an example of an abnormal wall condition. The dangers related to flow blockages or functional occlusions resulting from the disease have made atherosclerosis the focus of many disclosed devices. Such devices can be categorized by their structures and tissue treatment mechanisms. These categories may include direct contact electrode devices, resistance heating devices, light transmission/conversion-to-heat devices, hot fluid lumen devices, and radio frequency (RF) heated devices.

Several direct (or nearly direct) contact electrode devices have been disclosed. U.S. Pat. No. 4,998,933 to Eggers et al. describes a catheter designed for thermal angioplasty which utilizes a heated electrode in direct contact with surrounding tissue or plaque deposits as a mechanism for treating the diseased lumen walls. U.S. Pat. Nos. 4,676,258 to InoKuchi et al. and 4,807,620 to Strul et al. disclose devices designed to treat surrounding tissues using heat generated by two electrodes within the device and an RF power source.

U.S. Pat. Nos. 4,672,962 to Hershenson and 5,035,694 to Kasprzyk et al. disclose devices which may be categorized as resistance heating probes. In each of these devices, current flowing through a conductive material at the end of the device provides heat which is transmitted to surrounding tissues for treatment of atherosclerosis and other diseases. Current is transmitted in each of these devices by electrically conductive materials. In contrast, U.S. Pat. No. 5,226,430 to Spears et al. discloses a device which uses light transmitting fiber to transmit energy to a heat generating element at the tip of the device. The heat generating element in that device transmits heat energy to a surrounding balloon structure which is in contact with surrounding tissue. In further contrast, U.S. Pat. No. 4,790,311 to Ruiz discloses an angioplasty catheter system wherein a heat generating electrode at the tip of the device is heated using the transmission of RF energy. This device may be categorized as an RF heated device.

U.S. Pat. Nos. 5,190,540 and 5,292,321 to Lee can be categorized as hot fluid lumen devices. In the '540 disclosure, Lee describes a balloon catheter designed for remodelling a body lumen. This device utilizes a multilumen catheter which is capable of delivering heated fluid to an expandable balloon lumen, thereby expanding the balloon geometrically and heating tissue which is in contact with the balloon. In the '321 disclosure, Lee describes a similar device wherein the lumen of an expandable balloon is filled with thermoplastic material which is designed to become softer and more moldable when heated by a heating element.

Endometriosis, another abnormal wall tissue condition, is associated with the endometrial cavity of the female. This medical condition, characterized by dangerously proliferative uterine wall tissue along the surface of the endometrial cavity, has been treated by delivering energy to the tissue. U.S. Pat. No. 5,449,380 to Chin discloses a medical device for delivering energy to the wall tissue of a diseased endometrial cavity using a balloon lumen with heated fluid circulating therein. Other devices, such as those disclosed in U.S. Pat. Nos. 5,505,730 to Edwards; 5,558,672 to Edwards et al. and 5,562,720 to Stern et al. are designed for treating particular tissues using heat generated by the flow of RF current between electrodes.

Diseased or structurally damaged blood vessels may bring about various abnormal wall conditions. The inducement of thrombosis and control of hemorrhaging within certain body lumens such as vessels have been the focus of several disclosed devices which use catheter-based heat sources for cauterizing damaged tissues. In U.S. Pat. No. 4,449,528, for example, Auth et al. disclose a thermal cautery probe designed for heating specific layers of tissue without producing deep tissue damage. The mechanism of heat generation in this device is a resistive coil within the cautery probe which is electrically connected to a power source. In U.S. Pat. No. 4,662,368, Hussein et al. disclose a device designed for localized heat application within a lumen. In this device, energy for heat generation is delivered to the tip of the device in the form of light by a flexible fiber. Heat from an element which converts light energy to heat energy is then conducted to the adjacent tissue. In U.S. Pat. No. 4,522,205, Taylor et al. disclose a device designed for inducing thrombosis in a blood vessel comprising an array of electrodes mounted onto an expandable balloon which may be delivered by a catheter. The inventors of this device hypothesize that when direct current flows through electrodes which are in contact with adjacent tissues, thrombosis is precipitated.

Maintenance of patency in diseased lumens such as blood vessels has been the focus of several disclosed devices, several of which may be characterized as cardiovascular stents. U.S. Pat. No. 5,078,736 to Behl, for example, discloses an apparatus for maintaining patency in the body passages comprising a stent structure which may be connected to a radiofrequency power source. In addition to mechanically supporting a body lumen, this device may provide for thermal disruption of the adjacent tissues which may inhibit reocclusion of the lumen. U.S. Pat. No. 5,178,618 to Kandarpa discloses a similar device which may be used for recanalizing an occluded vessel prior to mechanically supporting a lumen region.

Atrial Fibrillation

Cardiac arrhythmias, and atrial fibrillation in particular, persist as common and dangerous medical ailments, especially in the aging population. In patients with normal sinus rhythm, the heart, which is comprised of atrial, ventricular, and excitatory conduction tissue, is electrically excited to beat in a synchronous, patterned fashion. In patients with cardiac arrhythmia, abnormal regions of cardiac tissue do not follow the synchronous beating cycle associated with normally conductive tissue in patients with sinus rhythm. Instead, the abnormal regions of cardiac tissue aberrantly conduct to adjacent tissue, thereby disrupting the cardiac cycle into an asynchronous cardiac rhythm. Such abnormal conduction has been previously known to occur at various regions of the heart, such as for example in the region of the sino-atrial (SA) node, along the conduction pathways of the atrioventricular (AV) node and the Bundle of His, or in the cardiac muscle tissue forming the walls of the ventricular and atrial cardiac chambers.

Cardiac arrhythmias, including atrial arrhythmia, may be of a multiwavelet reentrant type, characterized by multiple asynchronous loops of electrical impulses that are scattered about the atrial chamber and are often self propagating. In the alternative or in addition to the multiwavelet reentrant type, cardiac arrhythmias may also have a focal origin, such as when an isolated region of tissue in an atrium fires autonomously in a rapid, repetitive fashion. Cardiac arrhythmias, including atrial fibrillation, may be generally detected using the global technique of an electrocardiogram (EKG). More sensitive procedures of mapping the specific conduction along the cardiac chambers have also been disclosed, such as for example in U.S. Pat. Nos. 4,641,649 to Walinsky et al. and WO 96/32897 to Desai.

A host of clinical conditions may result from the irregular cardiac function and resulting hemodynamic abnormalities associated with atrial fibrillation, including stroke, heart failure, and other thromboembolic events. In fact, atrial fibrillation is believed to be a significant cause of cerebral stroke, wherein the abnormal hemodynamics in the left atrium caused by the fibrillatory wall motion precipitate the formation of thrombus within the atrial chamber. A thromboembolism is ultimately dislodged into the left ventricle, which thereafter pumps the embolism into the cerebral circulation where a stroke results. Accordingly, numerous procedures for treating atrial arrhythmias have been developed, including pharmacological, surgical, and catheter ablation procedures.

Conventional Atrial Arrhythmia Treatments

Several pharmacological approaches intended to remedy or otherwise treat atrial arrhythmias have been disclosed, such as, for example, in U.S. Pat. No. 4,673,563 to Berne et al.; U.S. Pat. No. 4,569,801 to Molloy et al.; and also by Hindricks, et al. in "Current Management of Arrhythmias" (1991). However, such pharmacological solutions are not generally believed to be entirely effective in many cases, and may in some cases result in proarrhythmia and long term inefficacy.

Several surgical approaches have also been developed with the intention of treating atrial fibrillation. One particular example is known as the "maze procedure," as is disclosed by Cox, JL et al. in "The surgical treatment of atrial fibrillation. I. Summary" *Thoracic and Cardiovascular Surgery* 101(3), pp. 402–405 (1991); and also by Cox, JL in "The surgical treatment of atrial fibrillation. IV. Surgical Technique", *Thoracic and Cardiovascular Surgery* 101(4), pp. 584–592 (1991). In general, the "maze" procedure is designed to relieve atrial arrhythmia by restoring effective atrial systole and sinus node control through a prescribed pattern of incisions about the tissue wall. In the early clinical experiences reported, the "maze" procedure included surgical incisions in both the right and the left atrial chambers. However, more recent reports predict that the surgical "maze" procedure may be substantially efficacious when performed only in the left atrium, such as is disclosed in Sueda et al., "Simple Left Atrial Procedure for Chronic Atrial Fibrillation Associated With Mitral Valve Disease" (1996).

The "maze procedure" as performed in the left atrium generally includes forming vertical incisions from the two superior pulmonary veins and terminating in the region of the mitral valve annulus, traversing the inferior pulmonary veins en route. An additional horizontal line also connects the superior ends of the two vertical incisions. Thus, the atrial wall region bordered by the pulmonary vein ostia is isolated from the other atrial tissue. In this process, the mechanical sectioning of atrial tissue eliminates the precipitating conduction to the atrial arrhythmia by creating conduction blocks within the aberrant electrical conduction pathways.

While the "maze" procedure as reported by Cox and others, and also other surgical procedures, have met some success in treating patients with atrial arrhythmia, its highly invasive methodology is believed to be prohibitive in most cases. However, these procedures have provided a guiding principle that mechanically isolating faulty cardiac tissue may successfully prevent atrial arrhythmia, and particularly atrial fibrillation caused by perpetually wandering reentrant wavelets or focal regions of arrhythmogenic conduction.

Modern Catheter Treatments for Atrial Arrhythmia

Success with surgical interventions through atrial segmentation, particularly with regard to the surgical "maze" procedure just described, has inspired the development of less invasive catheter-based approaches to treat atrial fibrillation through cardiac tissue ablation. Examples of such catheter-based devices and treatment methods have generally targeted atrial segmentation with ablation catheter devices and methods adapted to form linear or curvilinear lesions in the wall tissue which defines the atrial chambers, such as are disclosed in the following U.S. Patents: U.S. Pat. No. 5,617,854 to Munsif; U.S. Pat. No. 4,898,591 to Jang et al.; U.S. Pat. No. 5,487,385 to Avitall; and U.S. Pat. No. 5,582,609 to Swanson. The disclosures of these patents are herein incorporated in their entirety by reference thereto.

Additional examples of catheter-based tissue ablation in performing less-invasive cardiac chamber segmentation procedures are also disclosed in the following articles: "Physics and Engineering of Transcatheter Tissue Ablation", Avitall et al., *Journal of American College of Cardiology*, Volume 22, No. 3:921–932 (1993); and "Right and Left Atrial Radiofrequency Catheter Therapy of Paroxysmal Atrial Fibrillation," Haissaguerre, et al., *Journal of Cardiovascular Electrophysiology* 7(12), pp. 1132–1144 (1996). These articles are herein incorporated in their entirety by reference thereto. Furthermore, the use of particular guiding sheath designs for use in ablation procedures in both the right and/or left atrial chambers are disclosed in U.S. Pat. Nos. 5,427,119; 5,497,119; 5,564,440; 5,575,766 to Swartz et al. In addition, various energy delivery modalities have been disclosed for forming such atrial wall lesions, and include use of microwave, laser, and more commonly, radiofrequency energies to create conduction blocks along the cardiac tissue wall, as disclosed in U.S. Pat. Nos. WO 93/20767 to Stern et al.; 5,104,393 to Isner et al.; and 5,575,766 to Swartz et al, respectively. The disclosures of these references are herein incorporated in their entirety by reference thereto.

In addition to attempting atrial wall segmentation with long linear lesions for treating atrial arrhythmia, ablation catheter devices and methods have also been disclosed which are intended to ablate arrhythmogenic tissue of the left-sided accessory pathways, such as those associated with the Wolff-Parkinson-White syndrome, through the wall of an adjacent region along the coronary sinus.

For example, Fram et al., in "Feasibility of RF Powered Thermal Balloon Ablation of Atrioventricular Bypass Tracts via the Coronary Sinus: In vivo Canine Studies," *PACE*, Vol. 18, p 1518–1530 (1995), disclose attempted thermal ablation of left-sided accessory pathways in dogs using a balloon which is heated with bipolar radiofrequency electrodes positioned within the balloon. A 10 French guiding catheter and a 0.035" wire were provided in an assembly adapted to advance the ablation catheter into the coronary sinus from the jugular vein. Thermal ablation procedures were performed in the posterospetal coronary sinus and in the left free-wall coronary sinus with thermal inflations at either 70 deg, 80 deg, or 90 deg for either 30 or 60 seconds. In all cases balloon occlusion was confirmed using distal dye injection. A compliant silicone balloon was used which had a diameter range of 5–20 mm and a length range of 8–23 mm over a final inflation pressure range of 0.4 to 1.5 atms. Fram et al. discloses that the lesion depth of some population groups may be sufficient to treat patients with Wolff-Parkinson-White syndrome.

Additional examples of cardiac tissue ablation from the region of the coronary sinus for the purpose of treating particular types of cardiac arrhythmias are disclosed in: "Long-term effects of percutaneous laser balloon ablation from the canine coronary sinus", Schuger CD et al., *Circulation* (1992) 86:947–954; and "Percutaneous laser balloon coagulation of accessory pathways", McMath LP et al., Diagn Ther Cardiovasc Interven 1991; 1425:165–171.

Focal Arrhythmias Originating from Pulmonary Veins

Atrial fibrillation may be focal in nature, caused by the rapid and repetitive firing of an isolated center within the atrial cardiac muscle tissue. These foci, defined by regions exhibiting a consistent and centrifugal pattern of electrical activation, may act as either a trigger of atrial fibrillatory paroxysmal or may even sustain the fibrillation. Recent studies have suggested that focal arrhythmia often originates from a tissue region along the pulmonary veins of the left atrium, and even more particularly in the superior pulmonary veins.

Less-invasive percutaneous catheter ablation techniques have been disclosed which use end-electrode catheter designs with the intention of ablating and thereby treating focal arrhythmias in the pulmonary veins. These ablation procedures are typically characterized by the incremental application of electrical energy to the tissue to form focal lesions designed to interrupt the inappropriate conduction pathways.

One example of a focal ablation method intended to destroy and thereby treat focal arrhythmia originating from a pulmonary vein is disclosed by Haissaguerre, et al. in "Right and Left Atrial Radiofrequency Catheter Therapy of Paroxysmal Atrial Fibrillation" in *Journal of Cardiovascular Electrophysiology* 7(12), pp. 1132–1144 (1996). Haissaguerre, et al. disclose radiofrequency catheter ablation of drug-refractory paroxysmal atrial fibrillation using linear atrial lesions complemented by focal ablation targeted at arrhythmogenic foci in a screened patient population. The site of the arrhythmogenic foci were generally located just inside the superior pulmonary vein, and were ablated using a standard 4 mm tip single ablation electrode.

In another focal ablation example, Jais et al. in "A focal source of atrial fibrillation treated by discrete radiofrequency ablation" *Circulation* 95:572–576 (1997) applies an ablative technique to patients with paroxysmal arrhythmias originating from a focal source. At the site of arrhythmogenic tissue, in both right and left atria, several pulses of a discrete source of radiofrequency energy were applied in order to eliminate the fibrillatory process.

None of the cited references discloses a circumferential ablation device assembly which is adapted to form a circumferential conduction block around the circumference of a pulmonary vein wall in order to treat focal left atrial arrhythmias originating in the pulmonary vein.

Nor do the cited references disclose a circumferential ablation device with a circumferential ablation element that forms an equatorial band along the working length of an expandable element which has a length that is substantially less that the working length of the expandable element.

Nor do the cited references disclose a circumferential ablation device with an expandable member which has a shape when expanded that is adapted to conform to a pulmonary vein ostium along a left ventricular wall.

Nor do the cited references disclose a circumferential ablation device with an ablation element which circumscribes a radially compliant expandable element and which is adapted to form a continuous circumferential lesion in tissue over a working range of expanded diameters.

Nor do the cited references disclose a circumferential ablation device assembly that is includes a circumferential ablation element on an expandable member and also a linear lesion ablation element adjacent to the expandable member.

SUMMARY OF THE INVENTION

The present invention is a circumferential ablation device assembly which is adapted to form a circumferential lesion along a circumferential path of tissue along a body space wall and which circumscribes a body space defined at least in part by the body space. The assembly includes an elongate body, an expandable member on the distal end portion of the elongate body which is adjustable from a radially collapsed position to a radially expanded position, and a circumferential ablation element that includes an equatorial or other circumferential band which circumscribes at least a portion of an outer surface of the working length of the expandable member when in the radially expanded position. The circumferential ablation element is adapted to ablate a circumferential region of tissue adjacent to the equatorial band and along the body space wall when the circumferential ablation element is coupled to and actuated by an ablation actuator.

In one variation, the equatorial band length is shorter than two-thirds the working length of the expandable member. In one mode of this variation, the ablation element includes a circumferential RF electrode in an RF ablation circuit. In another mode, the circumferential ablation electrode includes a porous membrane along the equatorial or other circumferential band which is adapted to pass electrically conductive fluid from the conductive fluid chamber and into tissue adjacent to the band, the fluid conducting current to the tissue in an RF ablation circuit. In still another mode, a thermal conductor is located along the equatorial band and is adapted to emit thermal energy into tissue adjacent to the equatorial band when the thermal conductor is coupled to and actuated by a thermal ablation actuator. In still a further mode, a pair of insulators may be positioned exteriorly of each of two ends of the circumferential ablation element, wherein the uninsulated space between the insulators forms the equatorial band which may be equatorially located or otherwise circumferentially located.

In another variation of the invention, a circumferential ablation member includes an expandable member with a working length which, when adjusted from a radially collapsed position to a radially expanded position, is adapted to conform to a pulmonary vein ostium. In one mode of this variation, the working length when expanded includes a taper with a distally reducing outer diameter from a proximal region to a distal region. In a further mode, the expandable member is radially compliant and is adapted to conform to the pulmonary vein ostium when the working length is expanded to the radially expanded position in the left atrium and the expandable member is thereafter forced retrogradedly against the pulmonary vein wall in the region of the pulmonary vein ostium.

In another variation of the invention, a circumferential ablation member includes an expandable member with a working length which is adjustable between a plurality of radially expanded positions each having a different expanded outer diameters in the region of the equatorial band. The equatorial band of the circumferential ablation element is adapted to ablate a continuous circumferential lesion pattern in tissue surrounding the equatorial band over the range of expanded outer diameters. In one mode of this variation, the equatorial band has a secondary shape along the outer surface of the working length, such as a modified step, serpentine, or sawtooth shape.

In another variation, the distal end portion of an elongate member includes a circumferential ablation member and also a linear ablation member having an elongate ablation element length and linear ablation element which is adapted to form a continuous linear lesion in tissue adjacent thereto when the linear ablation element is coupled to an ablation actuator. In a further mode of this variation, a first end of the linear ablation member is located adjacent to the expandable member which forms at least in part a first anchor adapted to secure the first linear ablation member end in the region of a pulmonary vein ostium along a left atrium wall. A second anchor is also provided adjacent to a second, opposite end of the linear ablation member end and is adapted to secure the second linear ablation member end to a second location along the left atrium wall.

BRIEF DESCRIPTION OF THE DRAWINGS

FIGS. 7A–B show perspective views of another circumferential ablation catheter variation during use in a left atrium according to the method of FIG. 2, wherein FIG. 7A shows a radially compliant expandable member with a working length adjusted to a radially expanded position while in the left atrium, and FIG. 7B shows the expandable member after advancing it into and engaging a pulmonary vein ostium while in the radially expanded position.

DETAILED DESCRIPTION OF THE EMBODIMENTS

As will be described with reference to the detailed embodiments below, the present invention is a circumferential ablation device assembly which is adapted to treat patients with atrial arrhythmia by forming a circumferential conduction block in a pulmonary vein which blocks electrical conduction along the longitudinal axis of the pulmonary vein wall and into the left atrium.

The terms "circumference" or "circumferential", including derivatives thereof, are herein intended to mean a continuous path or line which forms an outer border or perimeter that surrounds and thereby defines an enclosed region of space. Such a continuous path starts at one location along the outer border or perimeter, and translates along the outer border or perimeter until it is completed at the original starting location to enclose the defined region of space. The related term "circumscribe," including derivatives thereof, is herein intended to mean to enclose, surround, or encompass a defined region of space. Therefore, according to these defined terms, a continuous line which is traced around a region of space and which starts and ends at the same location "circumscribes" the region of space and has a "circumference" which is defined by the distance the line travels as it translates along the path circumscribing the space.

Still further, a circumferential path or element may include one or more of several shapes, and may be for example circular, oblong, ovular, elliptical, or otherwise planar enclosures. A circumferential path may also be three dimensional, such as for example two opposite-facing semi-circular paths in two different parallel or off-axis planes which are connected at their ends by line segments bridging between the planes.

Figure 1A:
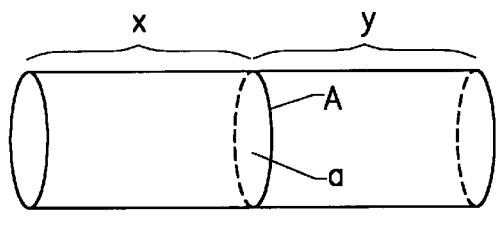
FIGS. 1A–E show schematic, perspective views of various exemplary circumferential conduction blocks formed in pulmonary vein wall tissue with the circumferential ablation device assembly of the present invention.
Figure 1B:
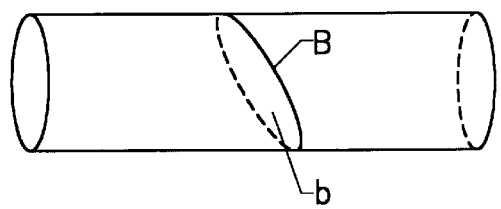
Figure 1C:
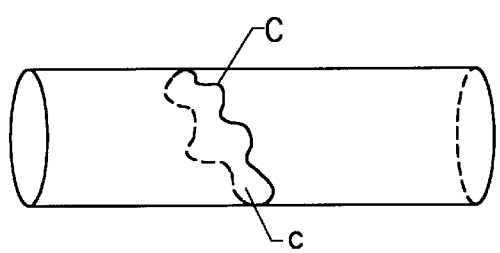
Figure 1D:
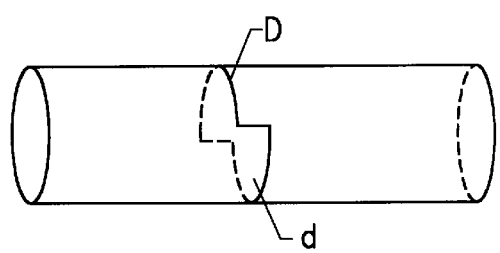
Figure 1E:
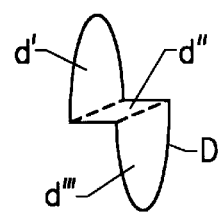

For purpose of further illustration, FIGS. 1A–D therefore show various circumferential paths A, B, C, and D, respectively, each translating along a portion of a pulmonary vein wall and circumscribing a defined region of space, shown at a, b, c, and d also respectively, each circumscribed region of space being a portion of a pulmonary vein lumen. For still further illustration of the three-dimensional circumferential case shown in FIG. 1D, FIG. 1E shows an exploded perspective view of circumferential path D as it circumscribes multiplanar portions of the pulmonary vein lumen shown at d', d", and d''', which together make up region d as shown in FIG. 1D.

The term "transect", including derivatives thereof, is also herein intended to mean to divide or separate a region of space into isolated regions. Thus, each of the regions circumscribed by the circumferential paths shown in FIGS. 1A–D transects the respective pulmonary vein, including its lumen and its wall, to the extent that the respective pulmonary vein is divided into a first longitudinal region located on one side of the transecting region, shown for example at region "X" in FIG. 1A, and a second longitudinal region on the other side of the transecting plane, shown for example at region "Y" also in FIG. 1A.

Therefore, a "circumferential conduction block" according to the present invention is formed along a region of tissue which follows a circumferential path along the pulmonary vein wall, circumscribing the pulmonary vein lumen and transecting the pulmonary vein relative to electrical conduction along its longitudinal axis. The transecting circumferential conduction block therefore isolates electrical conduction between opposite longitudinal portions of the pulmonary wall relative to the conduction block and along the longitudinal axis.

The terms "ablate" or "ablation," including derivatives thereof, are hereafter intended to mean the substantial altering of the mechanical, electrical, chemical, or other structural nature of tissue. In the context of intracardiac ablation applications shown and described with reference to the variations of the illustrative embodiment below, "ablation" is intended to mean sufficient altering of tissue properties to substantially block conduction of electrical signals from or through the ablated cardiac tissue.

The term "element" within the context of "ablation element" is herein intended to mean a discrete element, such as an electrode, or a plurality of discrete elements, such as a plurality of spaced electrodes, which are positioned so as to collectively ablate a region of tissue.

Therefore, an "ablation element" according to the defined terms may include a variety of specific structures adapted to ablate a defined region of tissue. For example, one suitable ablation element for use in the present invention may be formed, according to the teachings of the embodiments below, from an "energy emitting" type which is adapted to emit energy sufficient to ablate tissue when coupled to and energized by an energy source. Suitable "energy emitting" ablation elements for use in the present invention may therefore include, for example: an electrode element adapted to couple to a direct current ("DC") or alternating current ("AC") current source, such as a radiofrequency ("RF") current source; an antenna element which is energized by a microwave energy source; a heating element, such as a metallic element or other thermal conductor which is energized to emit heat such as by convective or conductive heat transfer, by resistive heating due to current flow, or by optical heating with light; a light emitting element, such as a fiber optic element which transmits light sufficient to ablate tissue when coupled to a light source; or an ultrasonic element such as an ultrasound crystal element which is adapted to emit ultrasonic sound waves sufficient to ablate tissue when coupled to a suitable excitation source.

In addition, other elements for altering the nature of tissue may be suitable as "ablation elements" under the present invention when adapted according to the detailed description of the invention below. For example, a cryoablation element adapted to sufficiently cool tissue to substantially alter the structure thereof may be suitable if adapted according to the teachings of the current invention. Furthermore, a fluid delivery element, such as a discrete port or a plurality of ports which are fluidly coupled to a fluid delivery source, may be adapted to infuse an ablating fluid, such as a fluid containing alcohol, into the tissue adjacent to the port or ports to substantially alter the nature of that tissue. The term "diagnose", including derivatives thereof, is intended to include patients suspected or predicted to have atrial arrhythmia, in addition to those having specific symptoms or mapped electrical conduction indicative of atrial arrhythmia.

In one aspect of using the circumferential ablation device assembly of the present invention, a patient diagnosed with multiple wavelet arrhythmia originating from multiple regions along the atrial wall is treated in part by forming the circumferential conduction block as an adjunct to forming long linear regions of conduction block between adjacent pulmonary vein ostia in a less-invasive "maze"-type catheter ablation procedure. More detail regarding particular ablation catheter embodiments adapted for use in such a method is provided below with reference to a combination circumferential-long linear lesion ablation device which is described below with reference to FIGS. 8A–D.

A patient diagnosed with focal arrhythmia originating from an arrhythmogenic origin or focus in a pulmonary vein may also be treated with the circumferential ablation device assembly of the present invention by using the assembly to form a circumferential conduction block along a circumferential path of pulmonary vein wall tissue that either includes the arrhythmogenic origin or is between the origin and the left atrium. In the former case, the arrhythmogenic tissue at the origin is destroyed by the conduction block as it is formed through that focus. In the latter case, the arrhythmogenic focus may still conduct abnormally, although such aberrant conduction is prevented from entering and affecting the atrial wall tissue due to the intervening circumferential conduction block.

Figure 2:
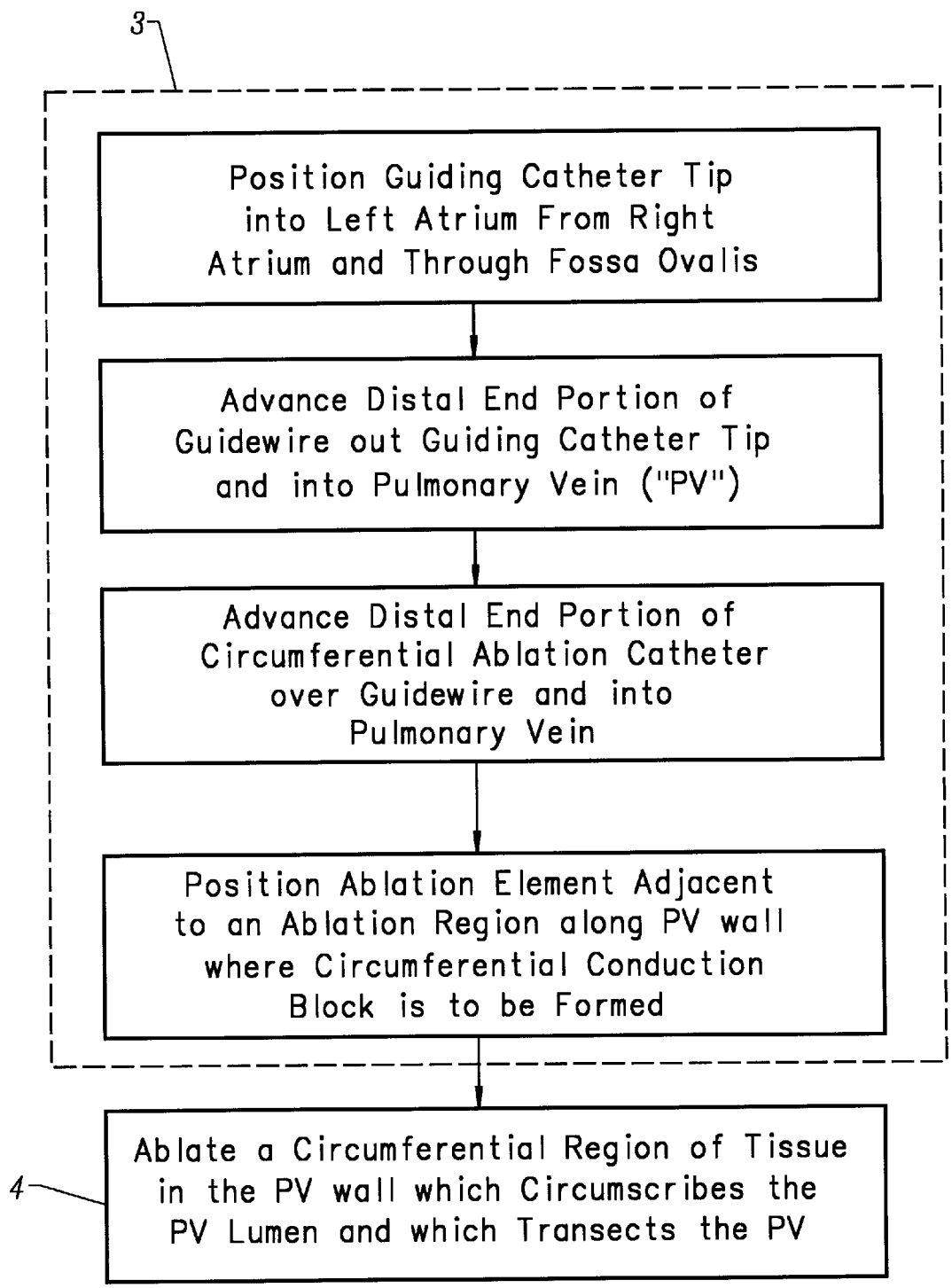
FIG. 2 shows a flow diagram of a method for using the circumferential ablation device assembly of the present invention.

FIG. 2 diagrammatically shows the sequential steps of a method for using the circumferential ablation device assembly of the present invention in forming a circumferential conduction block in a pulmonary vein. The circumferential ablation method according to FIG. 2 includes: positioning a circumferential ablation element at an ablation region along the pulmonary vein according to a series of detailed steps shown collectively in FIG. 2 as positioning step (3); and thereafter ablating a continuous circumferential region of tissue in the PV wall at the ablation region according to ablation step (4).

Further to positioning step (3) according to the method of FIG. 2, a distal tip of a guiding catheter is first positioned within the left atrium according to a transeptal access method, which is further described in more detail as follows. The right venous system is first accessed using the "Seldinger" technique, wherein a peripheral vein (such as a femoral vein) is punctured with a needle, the puncture wound is dilated with a dilator to a size sufficient to accommodate an introducer sheath, and an introducer sheath with at least one hemostatic valve is seated within the dilated puncture wound while maintaining relative hemostasis. With the introducer sheath in place, the guiding catheter or sheath is introduced through the hemostatic valve of the introducer sheath and is advanced along the peripheral vein, into the region of the vena cavae, and into the right atrium.

Once in the right atrium, the distal tip of the guiding catheter is positioned against the fossa ovalis in the intraatrial septal wall. A "Brochenbrough" needle or trocar is then advanced distally through the guide catheter until it punctures the fossa ovalis. A separate dilator may also be advanced with the needle through the fossa ovalis to prepare an access port through the septum for seating the guiding catheter. The guiding catheter thereafter replaces the needle across the septum and is seated in the left atrium through the fossa ovalis, thereby providing access for object devices through its own inner lumen and into the left atrium.

It is however further contemplated that other left atrial access methods may be suitable substitutes for using the circumferential ablation device assembly of the present invention. In one alternative variation not shown, a "retrograde" approach may be used, wherein the guiding catheter is advanced into the left atrium from the arterial system. In this variation, the Seldinger technique is employed to gain vascular access into the arterial system, rather than the venous, for example at a femoral artery. The guiding catheter is advanced retrogradedly through the aorta, around the aortic arch, into the ventricle, and then into the left atrium through the mitral valve.

Subsequent to gaining transeptal access to the left atrium as just described, positioning step (3) according to FIG. 2 next includes advancing a guidewire into a pulmonary vein, which is done generally through the guiding catheter seated in the fossa ovalis. In addition to the left atrial access guiding catheter, the guidewire according to this variation may also be advanced into the pulmonary vein by directing it into the vein with a second sub-selective delivery catheter (not shown) which is coaxial within the guiding catheter, such as for example by using one of the directional catheters disclosed in U.S. Pat. No. 5,575,766 to Swartz. Or, the guidewire may have sufficient stiffness and maneuverability in the left atrial cavity to unitarily subselect the desired pulmonary vein distally of the guiding catheter seated at the fossa ovalis.

Suitable guidewire designs for use in the overall circumferential ablation device assembly of the present invention may be selected from previously known designs, while generally any suitable choice should include a shaped, radiopaque distal end portion with a relatively stiff, torquable proximal portion adapted to steer the shaped tip under X-ray visualization. Guidewires having an outer diameter ranging from 0.010" to 0.035" may be suitable. In cases where the guidewire is used to bridge the atrium from the guiding catheter at the fossa ovalis, and where no other sub-selective guiding catheters are used, guidewires having an outer diameter ranging from 0.018" to 0.035" may be required. It is believed that guidewires within this size range may be required to provide sufficient stiffness and maneuverability in order to allow for guidewire control and to prevent undesirable guidewire prolapsing within the relatively open atrial cavity.

Subsequent to gaining pulmonary vein access, positioning step (3) of FIG. 2 next includes tracking the distal end portion of a circumferential ablation device assembly over the guidewire and into the pulmonary vein, followed by positioning a circumferential ablation element at an ablation region of the pulmonary vein where the circumferential conduction block is to be desirably formed.

Figure 3:
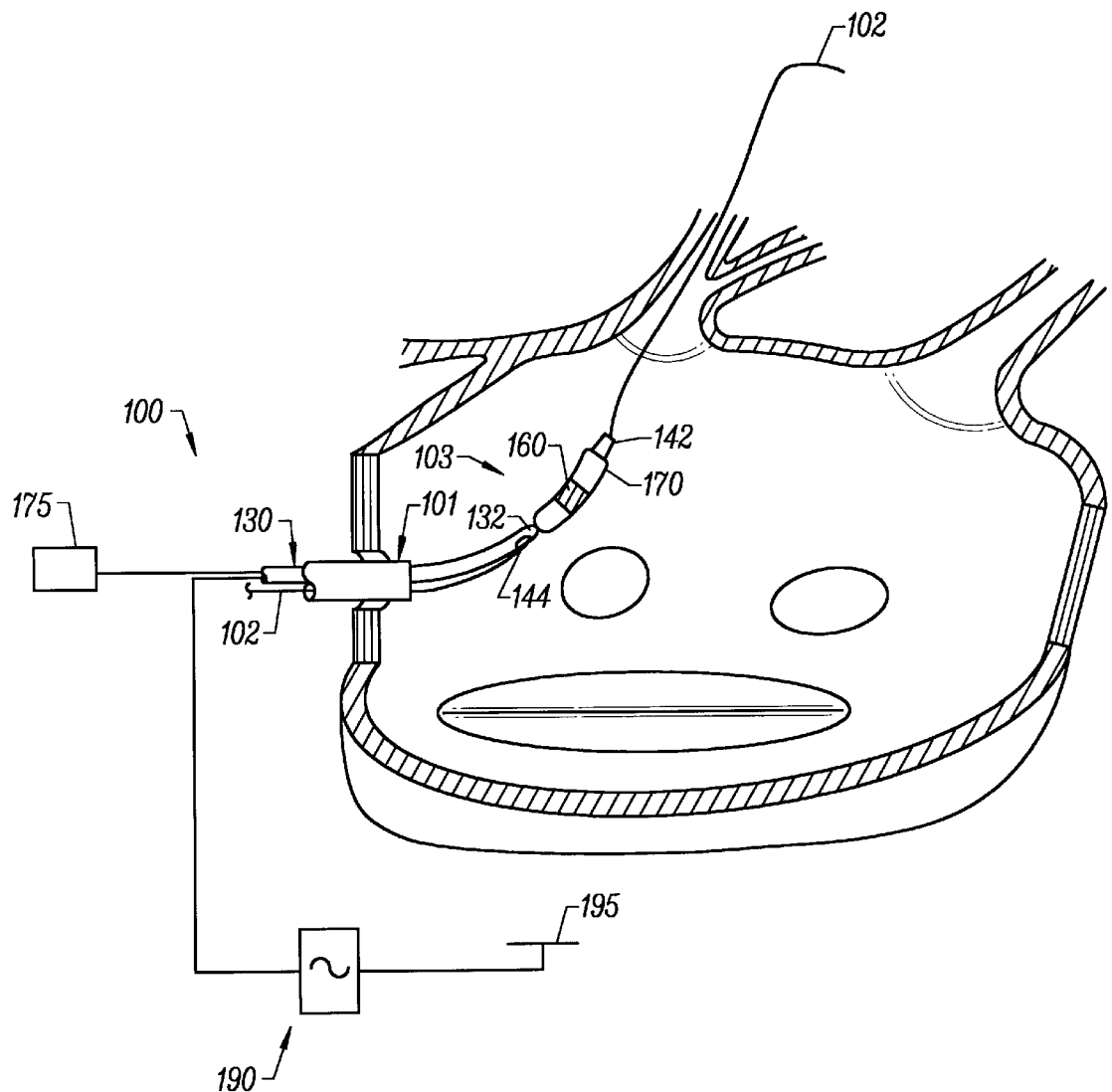
FIG. 3 shows a perspective view of a circumferential ablation device assembly during use in a left atrium subsequent to performing transeptal access and guidewire positioning steps according to the method of FIG. 2.
Figure 4:
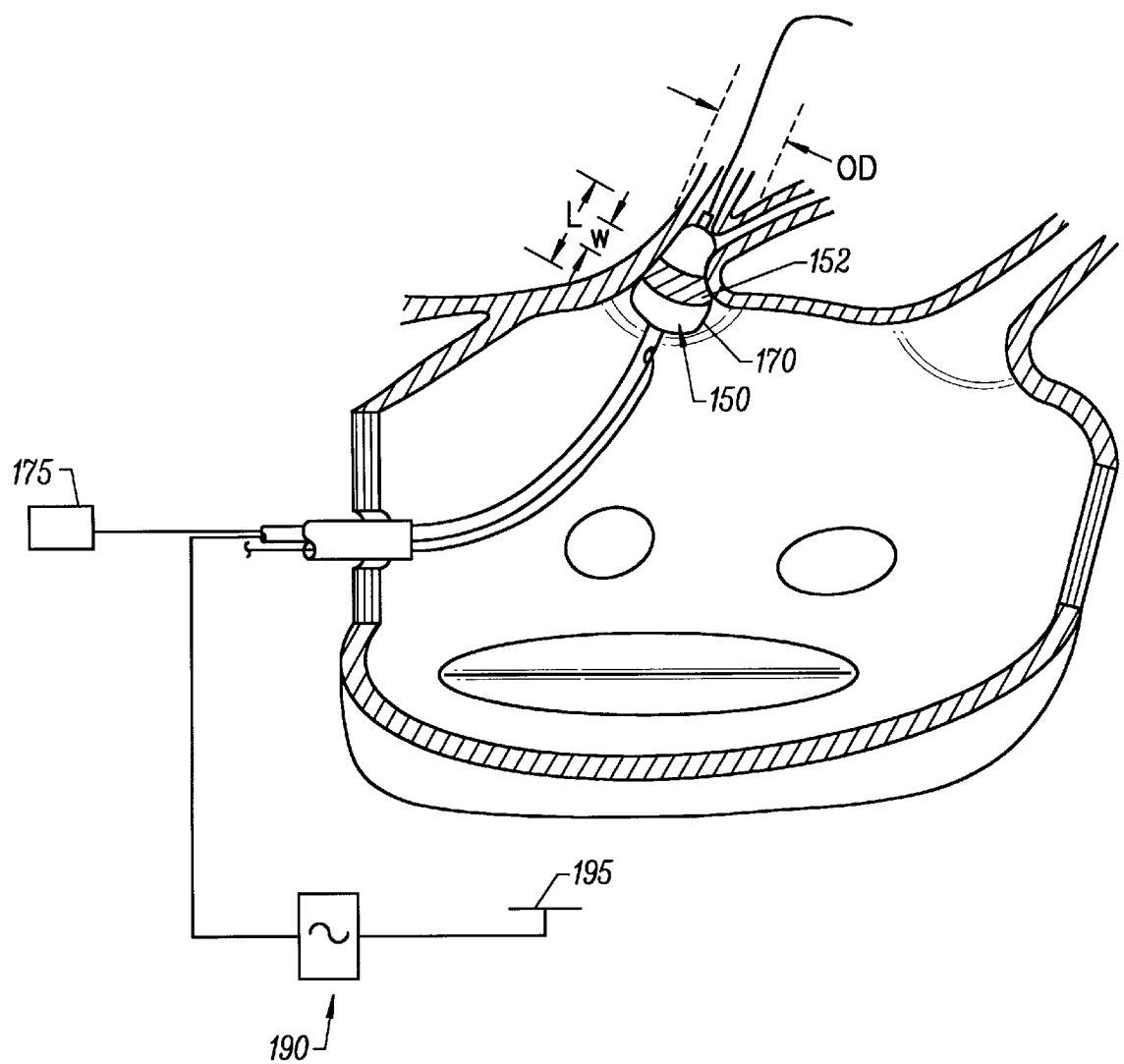
FIG. 4 shows a similar perspective view of the circumferential ablation device assembly shown in FIG. 3, and further shows a circumferential ablation catheter during use in ablating a circumferential region of tissue along a pulmonary vein wall to form a circumferential conduction block in the pulmonary vein according to the method of FIG. 2.

FIGS. 3–4 further show a circumferential ablation device assembly (100) according to the present invention during use in performing positioning step (3) and ablation step (4) just described with reference to FIG. 2. Included in the circumferential ablation device assembly (100) are guiding catheter (101), guidewire (102), and circumferential ablation catheter (103).

More specifically, FIG. 3 shows guiding catheter (101) subsequent to performing a transeptal access method according to FIG. 2, and also shows guidewire (102) subsequent to advancement and positioning within a pulmonary vein, also according to step (3) of FIG. 2. FIG. 3 shows circumferential ablation catheter (103) as it tracks coaxially over guidewire (102) with a distal guidewire tracking member, which is specifically shown only in part at first and second distal guidewire ports (142,144) located on the distal end portion (132) of an elongate catheter body (130). A guidewire lumen (not shown) extends between the first and second distal guidewire ports (142,144) and is adapted to slideably receive and track over the guidewire. In the particular variation of FIG. 3, the second distal guidewire port (142) is located on a distal end portion (132) of the elongate catheter body (130), although proximally of first distal guidewire port (142).

As would be apparent to one of ordinary skill, the distal guidewire tracking member shown in FIG. 3 and just described may be slideably coupled to the guidewire externally of the body in a "backloading" technique after the guidewire is first positioned in the pulmonary vein. Furthermore, there is no need in this guidewire tracking variation for a guidewire lumen in the proximal portions of the elongate catheter body (130), which allows for a reduction in the outer diameter of the catheter shaft in that region. Nevertheless, it is further contemplated that a design which places the second distal guidewire port on the proximal end portion of the elongate catheter body would also be acceptable, as is described below for example with reference to the perfusion embodiment of FIG. 5.

In addition, the inclusion of a guidewire lumen extending within the elongate body between first and second ports, as provided in FIG. 3, should not limit the scope of acceptable guidewire tracking members according to the present invention. Other guidewire tracking members which form a bore adapted to slideably receive and track over a guidewire are also considered acceptable, such as for example the structure adapted to engage a guidewire as described in U.S. Pat. No. 5,505,702 to Arney, the entirety of which is hereby incorporated by reference herein.

While the assemblies and methods shown variously throughout the Figures include a guidewire coupled to a guidewire tracking member on the circumferential ablation catheter, other detailed variations may also be suitable for positioning the circumferential ablation element at the ablation region in order to form a circumferential conduction block there. For example, an alternative circumferential ablation catheter not shown may include a "fixed-wire"-type of design wherein a guidewire is integrated into the ablation catheter as one unit. In another alternative assembly, the same type of sub-selective sheaths described above with reference to U.S. Pat. No. 5,575,766 to Swartz for advancing a guidewire into a pulmonary vein may also be used for advancing a circumferential ablation catheter device across the atrium and into a pulmonary vein.

FIG. 3 also shows circumferential ablation catheter (103) with a circumferential ablation element (160) formed on an expandable member (170). The expandable member (170) is shown in FIG. 3 in a radially collapsed position adapted for percutaneous translumenal delivery into the pulmonary vein according to positioning step (3) of FIG. 2. However, expandable member (170) is also adjustable to a radially expanded position when actuated by an expansion actuator (175), as shown in FIG. 4. Expansion actuator (175) may include, but is not limited to, a pressurizeable fluid source. According to the expanded state shown in FIG. 4, expandable member (170) includes a working length L relative to the longitudinal axis of the elongate catheter body which has a larger expanded outer diameter OD than when in the radially collapsed position. Furthermore, the expanded outer diameter OD is sufficient to circumferentially engage the ablation region of the pulmonary vein. Therefore, the terms "working length" are herein intended to mean the length of an expandable member which, when in a radially expanded position, has an expanded outer diameter that is: (a) greater than the outer diameter of the expandable member when in a radially collapsed position; and (b) sufficient to engage a body space wall or adjacent ablation region surrounding the expandable member, at least on two opposing internal sides of the body space wall or adjacent ablation region, with sufficient surface area to anchor the expandable member.

Circumferential ablation element (160) also includes a circumferential band (152) on the outer surface of working length L which is coupled to an ablation actuator (190) at a proximal end portion of the elongate catheter body (shown schematically). After expandable member (170) is adjusted to the radially expanded position and at least a portion of working length L circumferentially engages the pulmonary vein wall in the ablation region, the circumferential band (152) of the circumferential ablation element (160) is actuated by ablation actuator (190) to ablate the surrounding circumferential path of tissue in the pulmonary vein wall, thereby forming a circumferential lesion that circumscribes the pulmonary vein lumen and transects the electrical conductivity of the pulmonary vein to block conduction in a direction along its longitudinal axis.

Figure 5B:
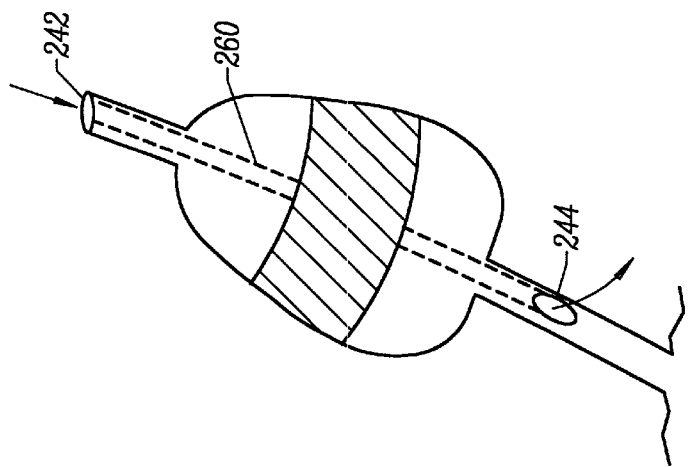
FIG. 5B is an enlarged partial view of the circumferential ablation catheter shown in FIG. 5A, with a perfusion lumen shown in phantom.
Figure 5A:
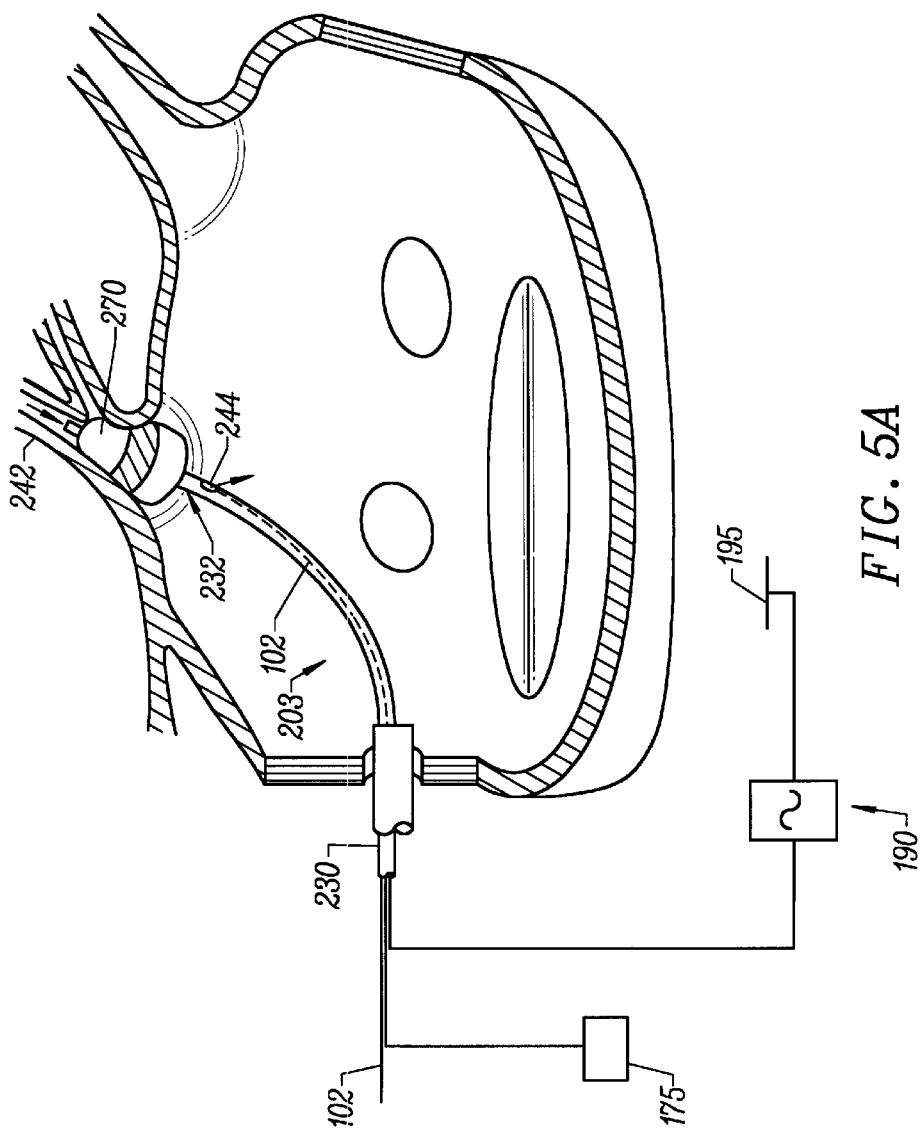
FIG. 5A shows a similar perspective view as shown in FIG. 4, although showing a further circumferential ablation catheter variation which is adapted to allow for blood perfusion from the pulmonary vein and into the atrium while performing the circumferential ablation method shown diagrammatically in FIG. 2.

FIG. 5A shows another circumferential ablation catheter (203) during use also according to the method of FIG. 2, wherein a perfusion lumen (260) (shown in phantom in FIG. 5B) is formed within the distal end portion (232) of elongate catheter body (230). The perfusion lumen (260) in this example is formed between a distal perfusion port, which in this example is the first distal guidewire port (242), and proximal perfusion port (244). Proximal perfusion port (244) is formed through the wall of the elongate catheter body (230) and communicates with the guidewire lumen (not shown) which also forms the perfusion lumen between the distal and proximal perfusion ports. In the particular design shown, after the guidewire has provided for the placement of the ablation element into the pulmonary vein, the guidewire is withdrawn proximally of the proximal perfusion port (244) (shown schematically in shadow) so that the lumen between the ports is clear for antegrade blood flow into the distal perfusion port (242), proximally along the perfusion lumen, out the proximal perfusion port (244) and into the atrium (perfusion flow shown schematically with arrows).

Further to the perfusion design shown in FIGS. 5A–B, guidewire (102) is positioned in a guidewire lumen which extends the entire length of the elongate catheter body (230) in an "over-the-wire"-type of design, which facilitates the proximal withdrawal of the guidewire to allow for perfusion while maintaining the ability to subsequently readvance the guidewire distally through the first distal guidewire port (242) for catheter repositioning. In one alternative variation not shown, the guidewire is simply withdrawn and disengaged from the second distal guidewire port (244), in which case the circumferential ablation catheter must generally be withdrawn from the body in order to recouple the distal guidewire tracking member with the guidewire.

In another alternative perfusion variation not shown which is a modification of the embodiment of FIG. 5A, a proximal perfusion port is provided as a separate and distinct port positioned between the second distal guidewire port (244) and the expandable member (270), which allows for proximal withdrawal of the guidewire to clear the guidewire lumen and thereby form a perfusion lumen between the first distal guidewire port and the proximal perfusion port. The guidewire of this alternative variation, however, remains engaged within the guidewire lumen between the second distal guidewire port and the proximal perfusion port.

Passive perfusion during expansion of the expandable member is believed to minimize stasis and allow the target pulmonary vein to continue in its atrial filling function during the atrial arrhythmia treatment procedure. Without this perfusion feature, the expandable member when in the radially expanded position during ablation blocks the flow from the vein into the atrium, which flow stasis may result in undesirable thrombogenesis in the pulmonary vein distally to the expandable member. In addition, in cases where the ablation element is adapted to ablate tissue with heat conduction at the ablation region, as described by reference to more detailed embodiments below, the perfusion feature according to the variation of FIGS. 5A–B may also provide a cooling function in the surrounding region, including in the blood adjacent to the expandable member.

Moreover, in addition to the specific perfusion structure shown and described by reference to FIGS. 5A–B, it is to be further understood that other structural variants which allow for perfusion flow during expansion of the expandable element may provide suitable substitutes according to one of ordinary skill without departing from the scope of the present invention.

Figure 6:
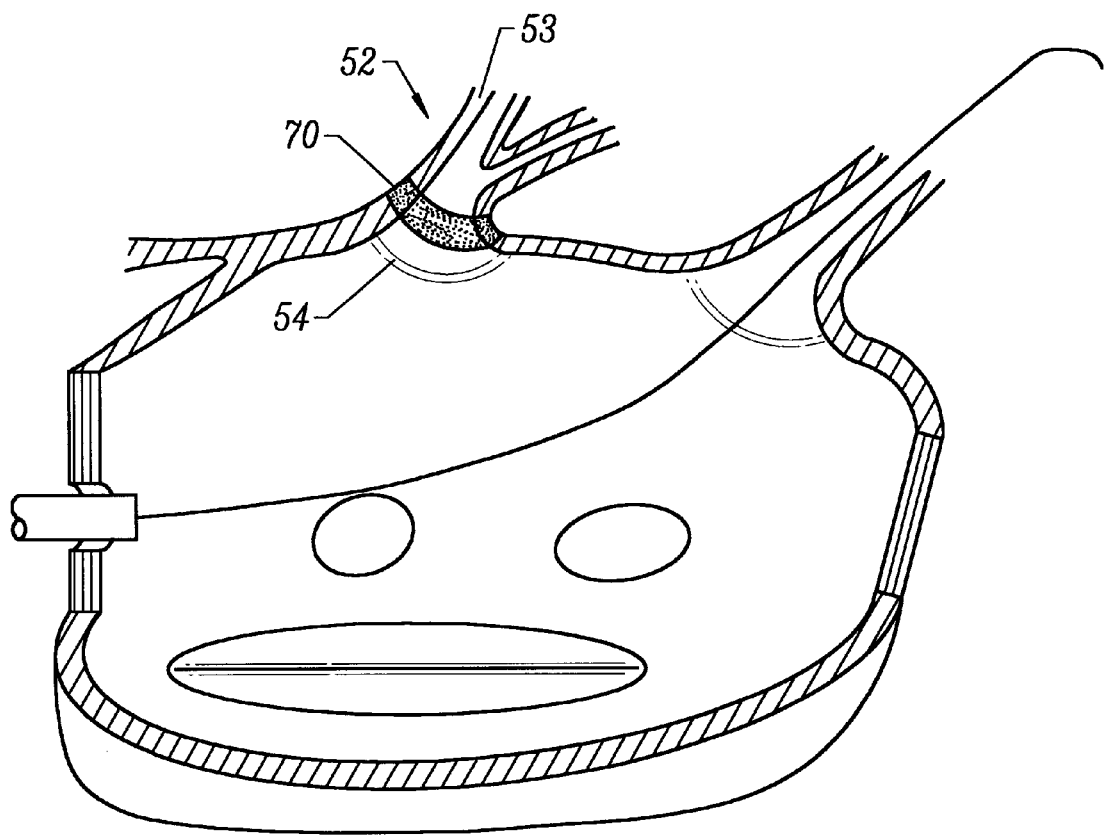
FIG. 6 shows a similar perspective view of the left atrium as that shown in FIGS. 3–5, although showing a cross-sectional view of a circumferential lesion after being formed by circumferential catheter ablation according to the method of FIG. 2.

FIG. 6 shows pulmonary vein (52) after removing the circumferential ablation device assembly subsequent to forming a circumferential lesion (70) around the ablation region of the pulmonary vein wall (53) according to the use of the circumferential ablation device assembly shown in stepwise fashion in FIGS. 3–6. Circumferential lesion (70) is shown located along the pulmonary vein adjacent to the pulmonary vein ostium (54), and is shown to also be "transmural," which is herein intended to mean extending completely through the wall, from one side to the other. Also, the circumferential lesion (70) is shown in FIG. 6 to form a "continuous" circumferential band, which is herein intended to mean without gaps around the pulmonary vein wall circumference, thereby circumscribing the pulmonary vein lumen.

It is believed, however, that circumferential catheter ablation with a circumferential ablation element according to the present invention may leave some tissue, either transmurally or along the circumference of the lesion, which is not actually ablated, but which is not substantial enough to allow for the passage of conductive signals. Therefore, the terms "transmural" and "continuous" as just defined are intended to have functional limitations, wherein some tissue in the ablation region may be unablated but there are no functional gaps which allow for symptomatically arrhythmogenic signals to conduct through the conduction block and into the atrium from the pulmonary vein.

Moreover, it is believed that the functionally transmural and continuous lesion qualities just described are characteristic of a completed circumferential conduction block in the pulmonary vein. Such a circumferential conduction block thereby transects the vein, isolating conduction between the portion of the vein on one longitudinal side of the lesion and the portion on the other side. Therefore, any foci of originating arrhythmogenic conduction which is opposite the conduction block from the atrium is prevented by the conduction block from conducting down into the atrium and atrial arrhythmic affects are therefore nullified.

Figure 7A:
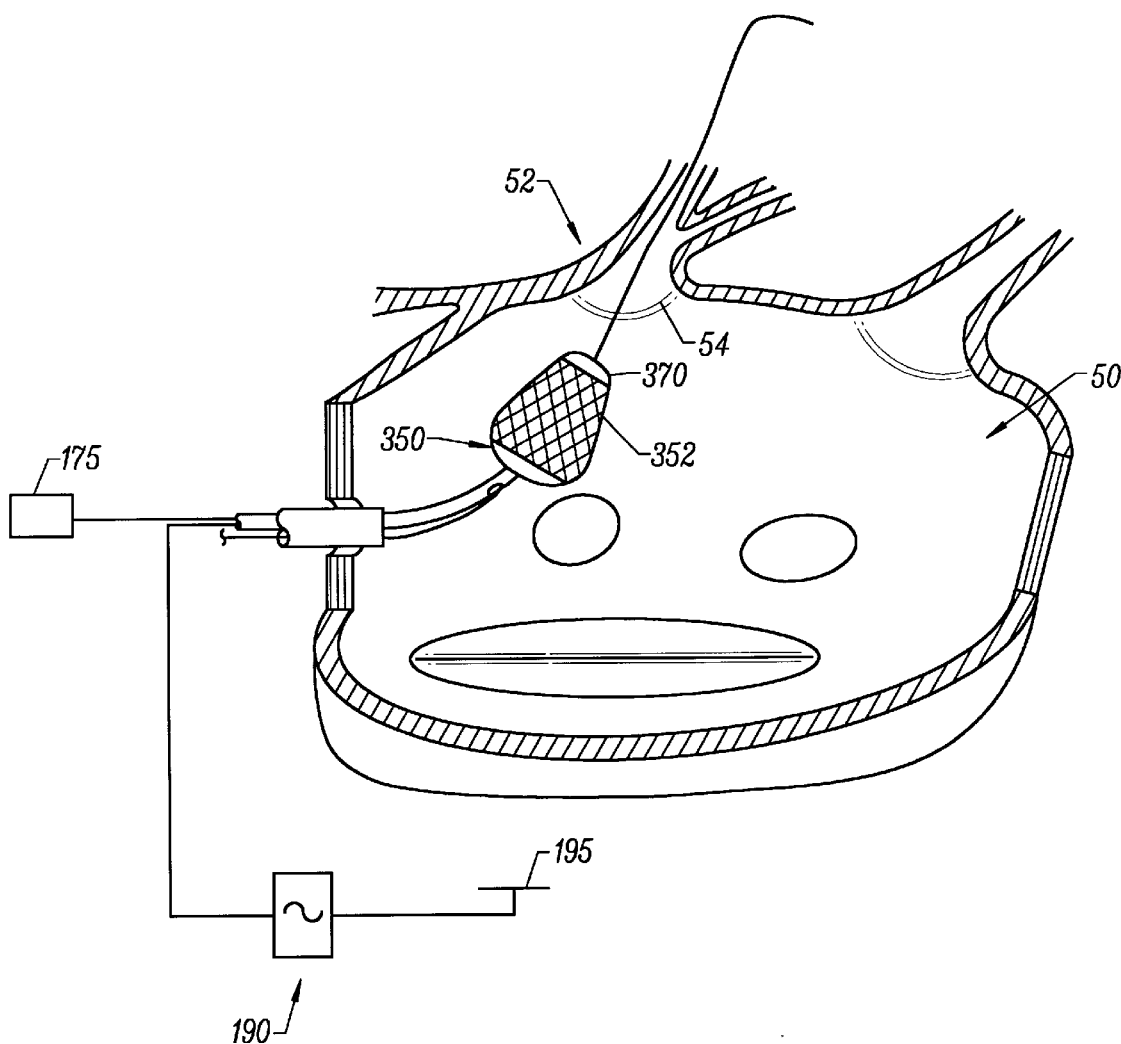
Figure 7B:
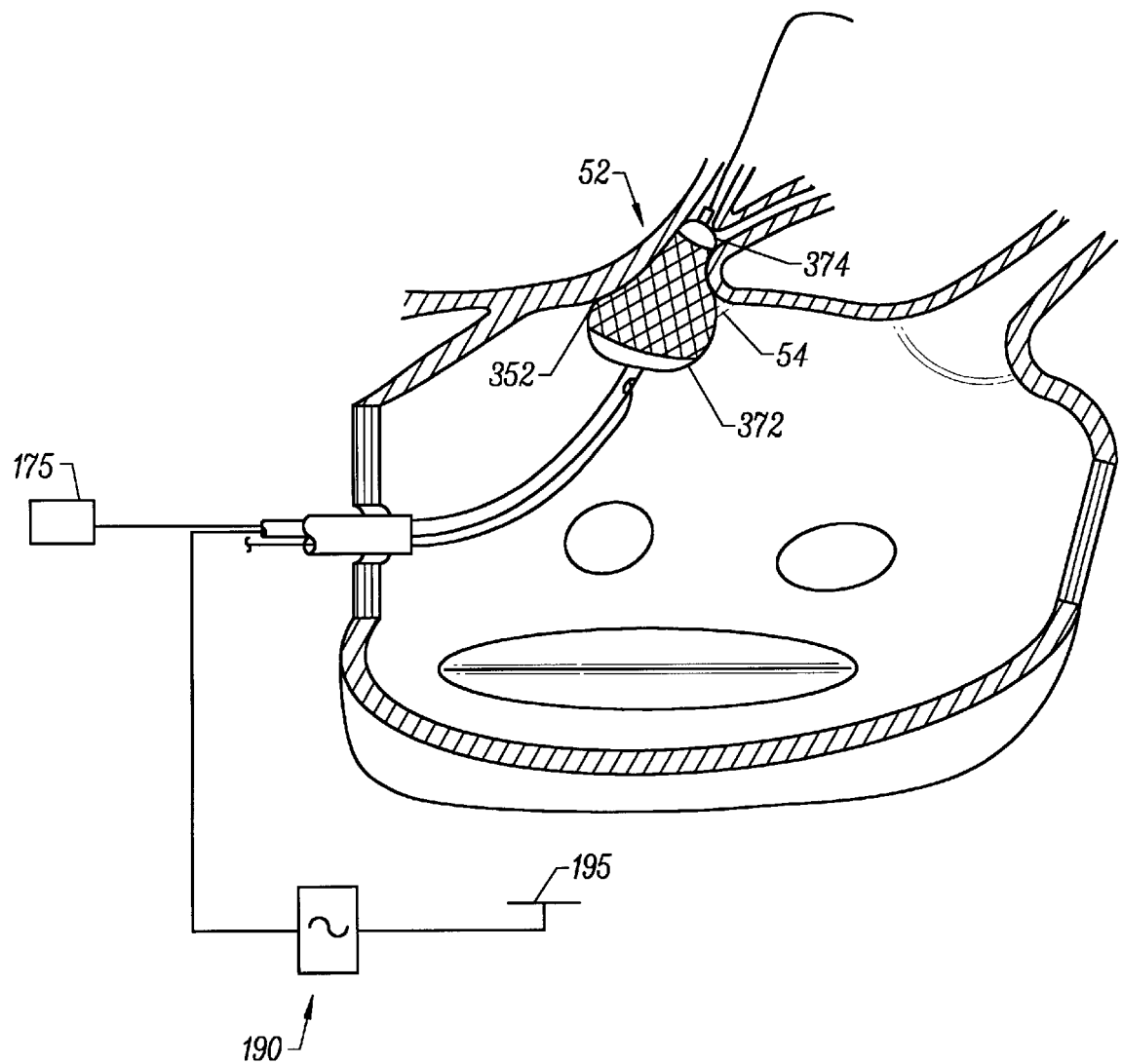
Figure 7C:
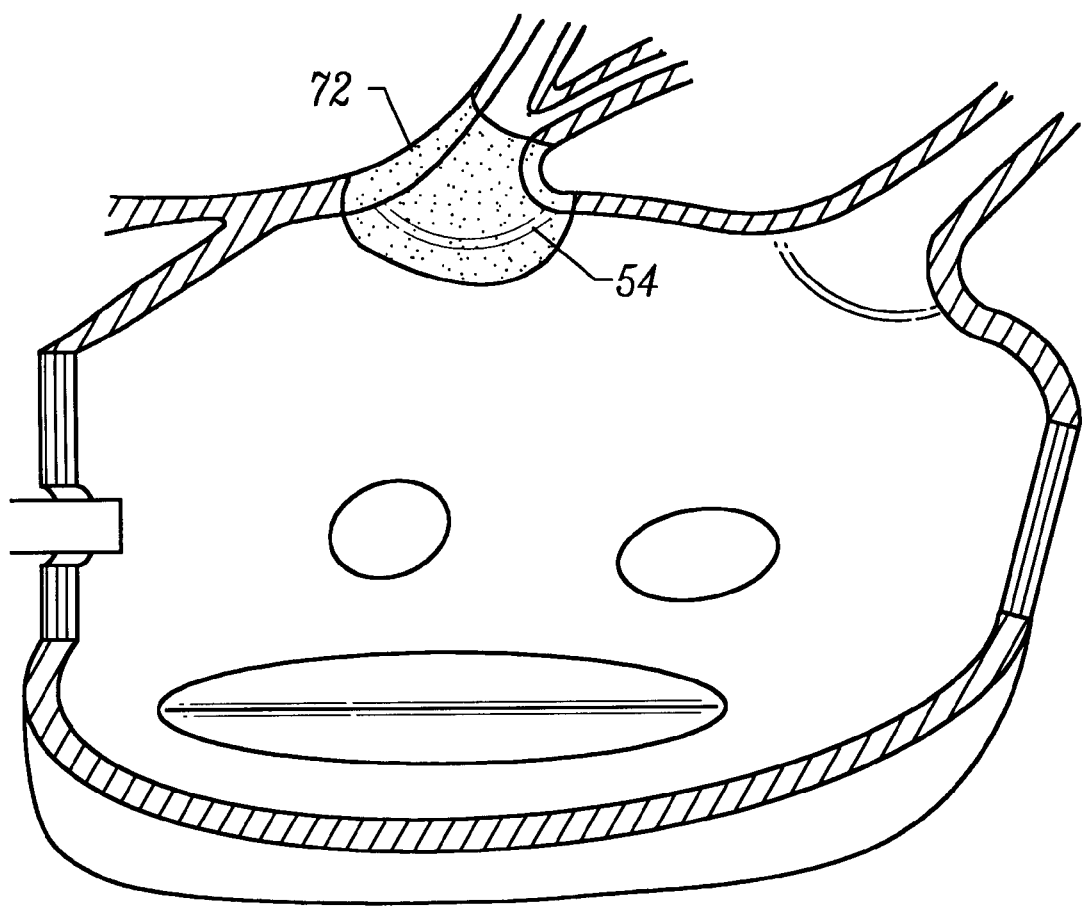
FIG. 7C shows the same perspective view of the left atrium shown in FIGS. 7A–B, although shown after forming a circumferential conduction block according to the circumferential ablation procedure of FIG. 2 and also after removing the circumferential ablation device assembly from the left atrium.

FIGS. 7A–B show a further variation of the present invention, wherein a circumferential ablation member (350) includes a radially compliant expandable member (370) which is adapted to conform to a pulmonary vein ostium (54) at least in part by adjusting it to a radially expanded position while in the left atrium and then advancing it into the ostium. FIG. 7A shows expandable member (370) after being adjusted to a radially expanded position while located in the left atrium (50). FIG. 7B further shows expandable member (370) after being advanced into the pulmonary vein (52) until at least a portion of the expanded working length L of circumferential ablation member (350), which includes a circumferential band (352), engages the pulmonary vein ostium (54). FIG. 7C shows a portion of a circumferential lesion (72) which forms a circumferential conduction block in the region of the pulmonary vein ostium (54) subsequent to actuating the circumferential ablation element to form the circumferential lesion.

FIGS. 8A–D collectively show a circumferential ablation device assembly according to the present invention as it is used to form a circumferential conduction block adjunctively to the formation of long linear lesions in a less-invasive "maze"-type procedure, as introduced above for the treatment of multiwavelet reentrant type fibrillation along the left atrial wall.

Figure 8A:
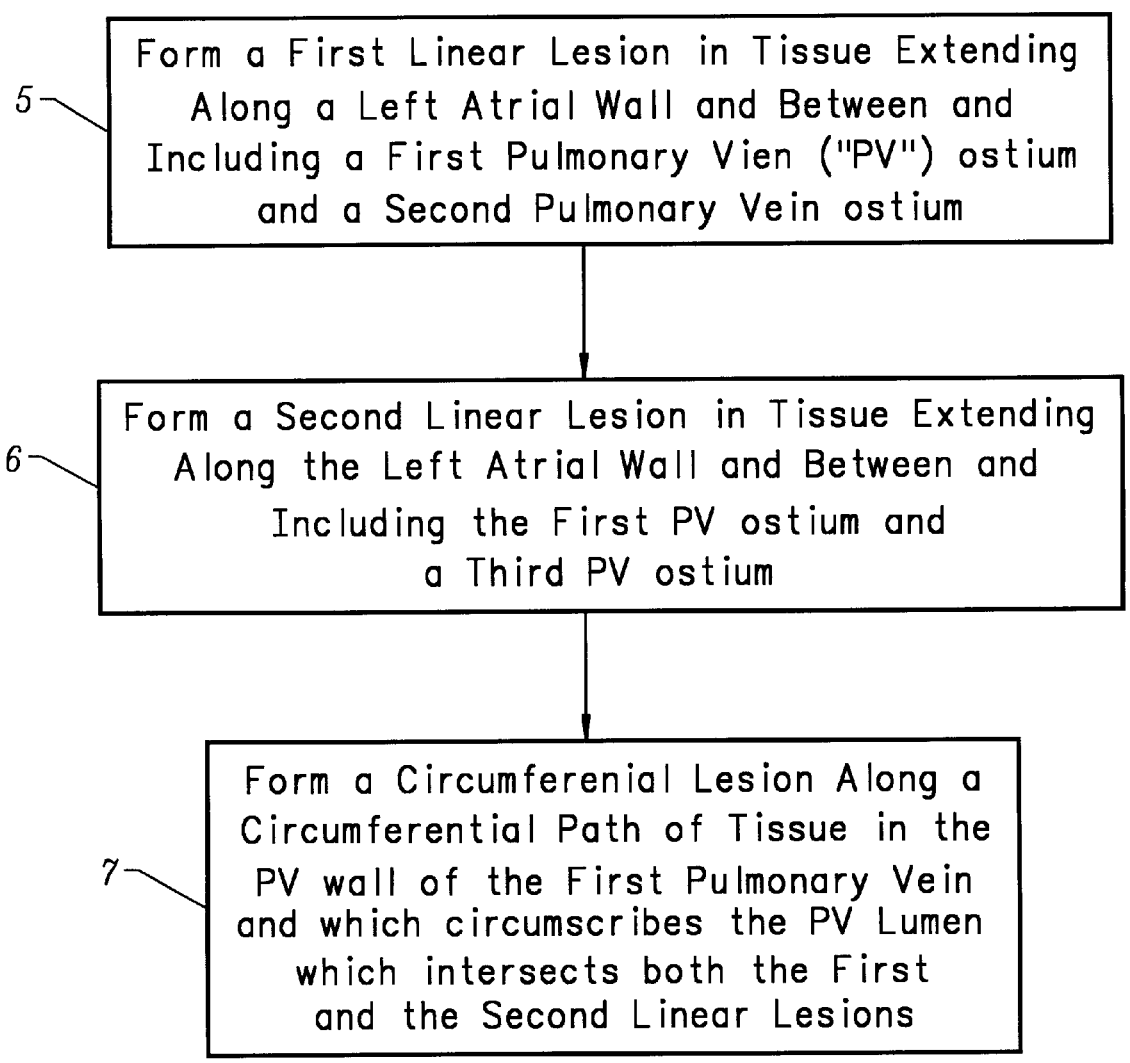
FIG. 8A diagrammatically shows a method for using the circumferential ablation device assembly of the present invention by forming a circumferential conduction block in a pulmonary vein in combination with a method for forming long linear lesions between pulmonary vein ostia in a less-invasive "maze"-type procedure.

More specifically, FIG. 8A diagrammatically shows a summary of steps for performing a "maze"-type procedure by forming circumferential conduction blocks that intersect with long linear conduction blocks formed between the pulmonary veins. As disclosed in copending patent application(Application Number not yet assigned) entitled "Tissue Ablation Device and Method of Use" filed by Michael Lesh, M.D. on May 9, 1997, which is herein incorporated in its entirety by reference thereto, a box-like conduction block surrounding an arrhythmogenic atrial wall region bounded by the pulmonary veins may be created by forming long linear lesions between anchors in all pairs of adjacent pulmonary vein ostia, such as is shown in part in steps (5) and (6) of FIG. 8A. However, it is further believed that, in some particular applications, such linear lesions may be made sufficiently narrow with respect to the surface area of the pulmonary vein ostia that they may not intersect, thereby leaving gaps between them which may present proarrhythmic pathways for abnormal conduction into and from the box, such as is shown between linear lesions (57,58) in FIG. 8B. Therefore, by forming the circumferential conduction block according to step (7) of FIG. 8A, and as shown by use of circumferential ablation member (450) in FIG. 8C, the linear lesions are thereby bridged and the gaps are closed.

Figure 8B:
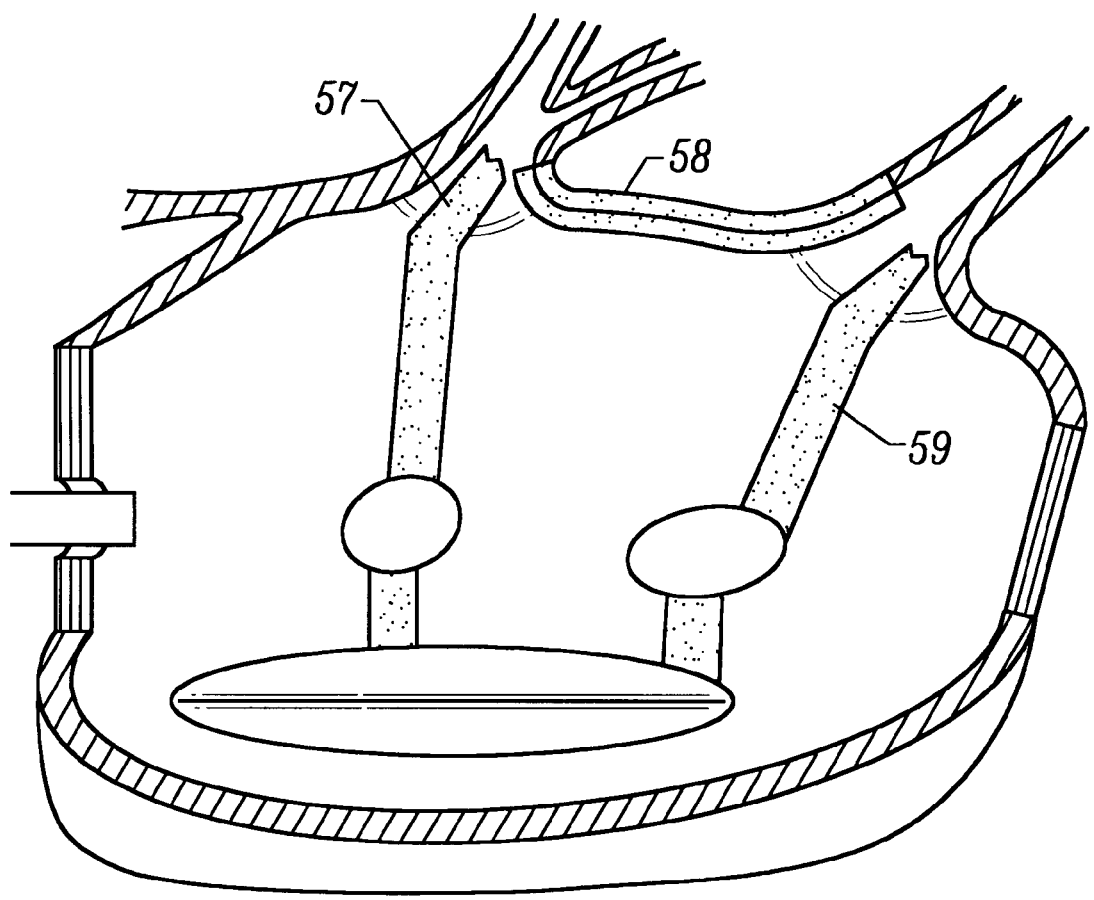
FIG. 8B shows a perspective view of a segmented left atrium after forming several long linear lesions between adjacent pairs of pulmonary vein ostia according to the method of FIG. 8A.
Figure 8C:
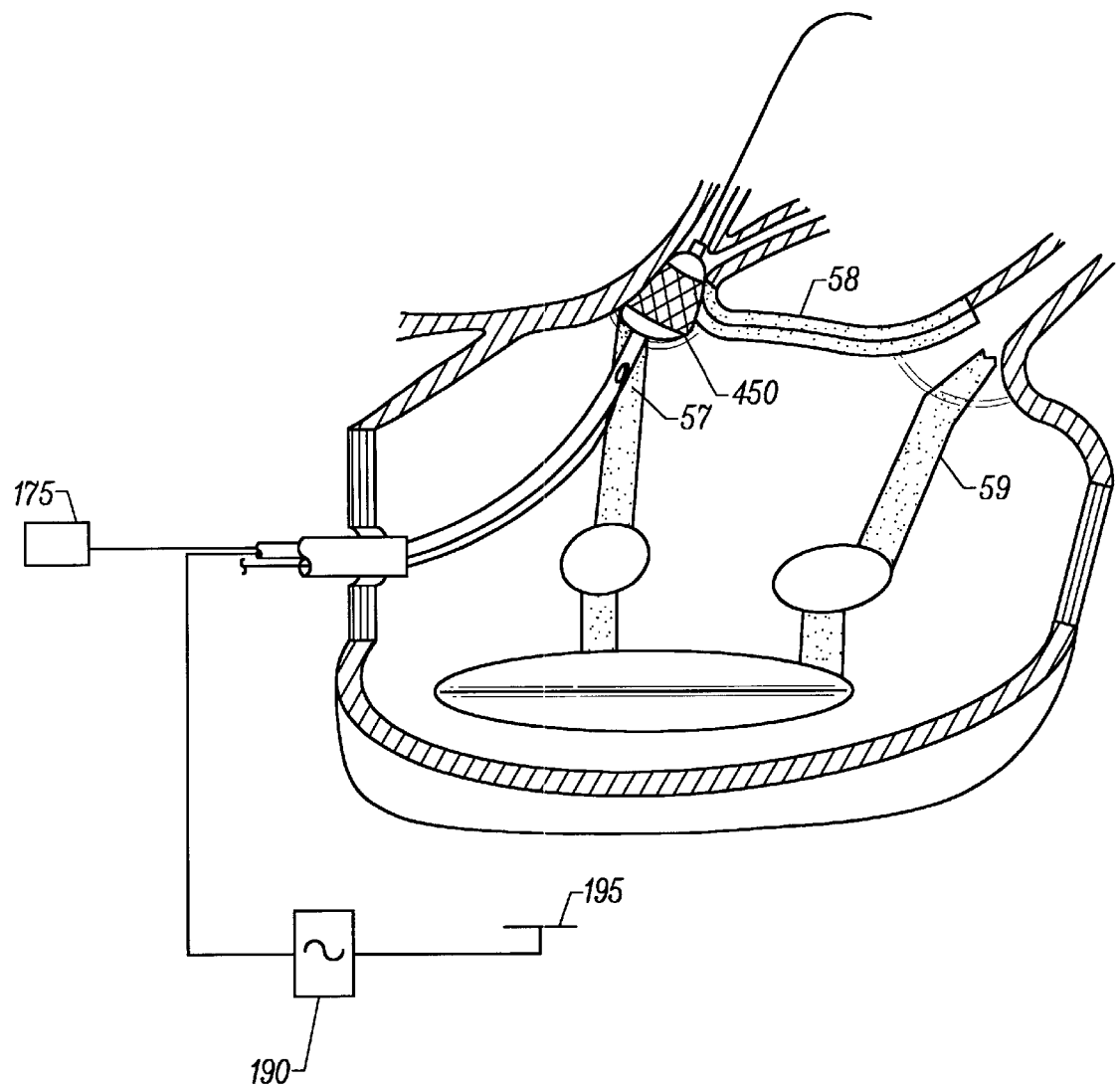
FIG. 8C shows a similar perspective view as that shown in FIG. 8B, although showing a circumferential ablation device assembly during use in forming a circumferential lesion in a pulmonary vein which intersects with two linear lesions that extend into the pulmonary vein, according to the method of FIG. 8A.
Figure 8D:
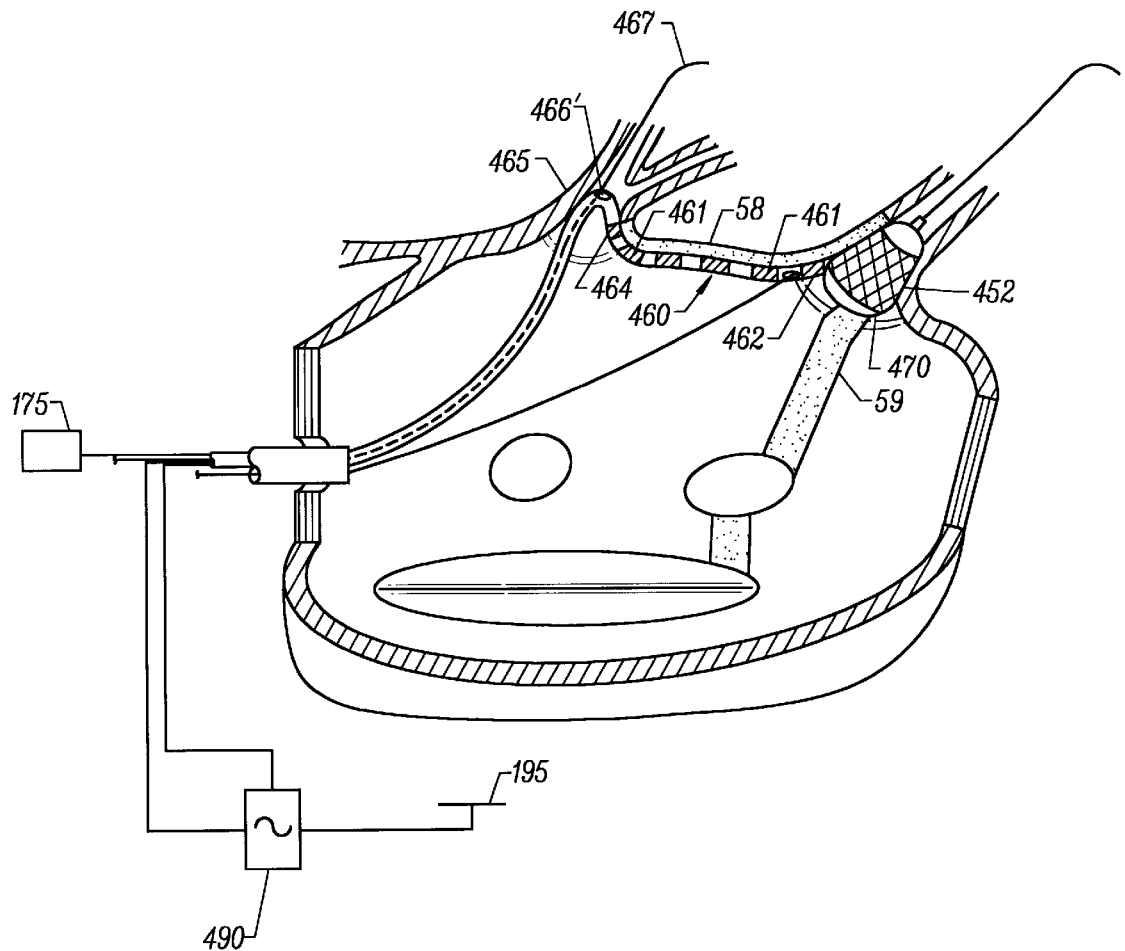
FIG. 8D shows a perspective view of another circumferential ablation catheter during use according to the method of FIG. 8A, wherein a circumferential ablation member is provided on an elongate catheter body adjacent to a linear ablation member such that circumferential and linear lesions formed in pulmonary vein wall tissue by the two ablation elements, respectively, intersect.

In a further variation to the specific embodiments shown in FIGS. 8B–C, FIG. 8D shows a circumferential ablation device assembly which includes both circumferential and linear ablation elements (452,460), respectively. Circumferential ablation member (450) is shown to include an expandable member (470) which is adjusted to a radially expanded position that is asymmetric to the underlying catheter shaft. Linear ablation member (460) extends along the elongate body proximally from the circumferential ablation member (450). When expanded sufficiently to engage the pulmonary vein wall, expandable member (470) provides at least a portion of an anchor for a first end (462) of linear ablation member (460).

A shaped stylet (466) is shown in shadow in FIG. 8D within the elongate catheter body in the region of the second end (464) of the linear ablation member (460). Shaped stylet (466) includes a port or opening (465) though which guidewire (469) passes in order to anchor the second end (464) into an adjacent pulmonary vein ostium such that the linear ablation member (460) is adapted to substantially contact the left atrial wall between the adjacent vein ostia to form the linear ablation according to the method of FIG. 8A. Alternatively to the use of shaped stylet (466) and guidewire (469), it is further contemplated that a second anchor may effected with, for example, an intermediate guidewire tracking member adapted to track over a guidewire (469) engaged to the pulmonary vein.

Figure 9:
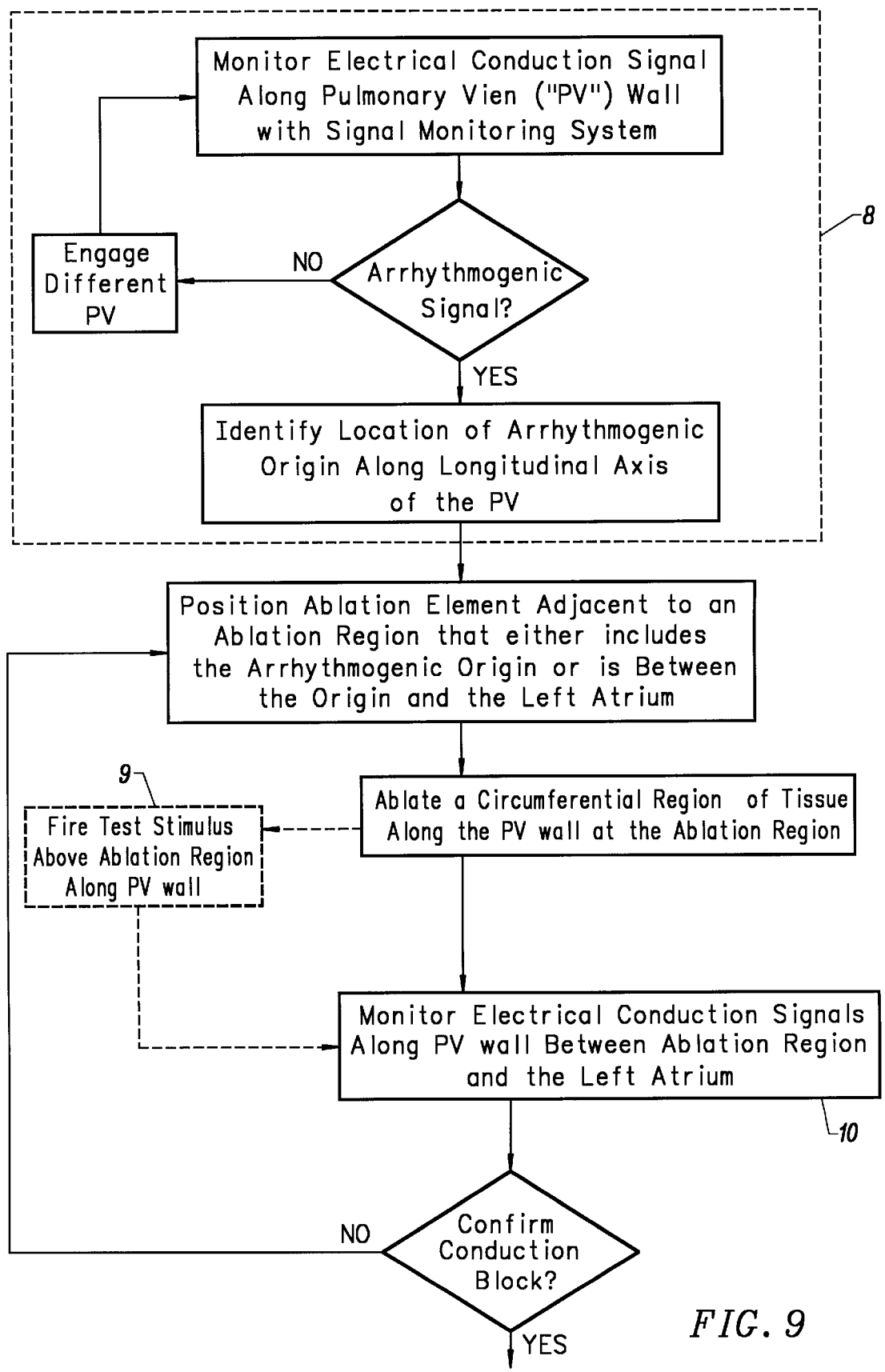
FIG. 9 diagrammatically shows a further method for using the circumferential ablation device assembly of the present invention to form a circumferential conduction block in a pulmonary vein wall, wherein signal monitoring and "post-ablation" test elements are used to locate an arrhythmogenic origin along the pulmonary vein wall and to test the efficacy of a circumferential conduction block in the wall, respectively.

FIG. 9 diagrammatically shows a further method for using the circumferential ablation device assembly of the present invention wherein electrical signals along the pulmonary vein are monitored with a sensing element before and after ablation according to steps (8) and (9), respectively. Signals within the pulmonary vein are monitored prior to forming a conduction block, as indicated in step (8) in FIG. 9, in order to confirm that the pulmonary vein chosen contains an arrhythmogenic origin for atrial arrhythmia. Failure to confirm an arrhythmogenic origin in the pulmonary vein, particularly in the case of a patient diagnosed with focal arrhythmia, may dictate the need to monitor signals in another pulmonary vein in order to direct treatment to the proper location in the heart. In addition, monitoring the pre-ablation signals may be used to indicate the location of the arrhythmogenic origin of the atrial arrhythmia, which information helps determine the best location to form the conduction block. As such, the conduction block may be positioned to include and therefore ablate the actual focal origin of the arrhythmia, or may be positioned between the focus and the atrium in order to block aberrant conduction from the focal origin and into the atrial wall.

In addition or in the alternative to monitoring electrical conduction signals in the pulmonary vein prior to ablation, electrical signals along the pulmonary vein wall may also be monitored by the sensing element subsequent to circumferential ablation, according to step (9) of the method of FIG. 9. This monitoring method aids in testing the efficacy of the ablation in forming a complete conduction block against arrhythmogenic conduction. Arrhythmogenic firing from the identified focus will not be observed during signal monitoring along the pulmonary vein wall when taken below a continuous circumferential and transmural lesion formation, and thus would characterize a successful circumferential conduction block. In contrast, observation of such arrhythmogenic signals between the lesion and the atrial wall characterizes a functionally incomplete or discontinuous circumference (gaps) or depth (transmurality) which would potentially identify the need for a subsequent follow-up procedure, such as a second circumferential lesioning procedure in the ablation region.

A test electrode may also be used in a "post ablation" signal monitoring method according to step (10) of FIG. 9. In one particular embodiment not shown, the test electrode is positioned on the distal end portion of an elongate catheter body and is electrically coupled to a current source for firing a test signal into the tissue surrounding the test electrode when it is placed distally or "upstream" of the circumferential lesion in an attempt to simulate a focal arrhythmia. This test signal generally challenges the robustness of the circumferential lesion in preventing atrial arrhythmia from any such future physiologically generated aberrant activity along the suspect vein.

Further to the signal monitoring and test stimulus methods just described, such methods may be performed with a separate electrode or electrode pair located on the catheter distal end portion adjacent to the region of the circumferential ablation element, or may be performed using one or more electrodes which form the circumferential ablation element itself, as will be further developed below.

Circumferential Ablation Member

The designs for the expandable member and circumferential ablation element for use in the circumferential ablation device assembly of the present invention have been described generically with reference to the embodiments shown in the previous Figures. Examples of more specific expandable member and ablation element embodiments which are adapted for use in the assembly of the present invention are further provided as follows.

Notwithstanding their somewhat schematic detail, the circumferential ablation members shown in the previous figures do illustrate one particular embodiment wherein a circumferential electrode element circumscribes an outer surface of an expandable member. The expandable member of the embodiments shown may take one of several different forms, although the expandable member is generally herein shown as an inflatable balloon that is coupled to an expansion actuator (175) which is a pressurizeable fluid source. The balloon is preferably made of a polymeric material and forms a fluid chamber which communicates with a fluid passageway (not shown in the figures) that extends proximally along the elongate catheter body and terminates proximally in a proximal fluid port that is adapted to couple to the pressurizeable fluid source.

In one expandable balloon variation, the balloon is constructed of a relatively inelastic polymer such as a polyethylene ("PE"; preferably linear low density or high density or blends thereof), polyolefin copolymer ("POC"), polyethylene terepthalate ("PET"), polyimide, or a nylon material. In this construction, the balloon has a low radial yield or compliance over a working range of pressures and may be folded into a predetermined configuration when deflated in order to facilitate introduction of the balloon into the desired ablation location via known percutaneous catheterization techniques. In this variation, one balloon size may not suitably engage all pulmonary vein walls for performing the circumferential ablation methods of the present invention on all needy patients. Therefore, it is further contemplated that a kit of multiple ablation catheters, with each balloon working length having a unique predetermined expanded diameter, may be provided from which a treating physician may chose a particular device to meet a particular patient's pulmonary vein anatomy.

In an alternative expandable balloon variation, the balloon is constructed of a relatively compliant, elastomeric material, such as, for example (but not limited to), a silicone, latex, or mylar elastomer. In this construction, the balloon takes the form of a tubular member in the deflated, non-expanded state. When the elastic tubular balloon is pressurized with fluid such as in the previous, relatively non-compliant example, the material forming the wall of the tubular member elastically deforms and stretches radially to a predetermined diameter for a given inflation pressure. It is further contemplated that the compliant balloon may be constructed as a composite, such as for example a latex or silicone balloon skin which includes fibers, such as metal, Kevlar, or nylon fibers, which are embedded into the skin. Such fibers, when provided in a predetermined pattern such as a mesh or braid, may provide a controlled compliance along a preferred axis, preferably limiting longitudinal compliance of the expandable member while allowing for radial compliance.

It is believed that, among other features, the relatively compliant variation may provide a wide range of working diameters, which may allow for a wide variety of patients, or of vessels within a single patient, to be treated with just one or a few devices. Furthermore, this range of diameters is achievable over a relatively low range of pressures, which is believed to diminish a potentially traumatic vessel response that may otherwise be presented concomitant with higher pressure inflations, particularly when the inflated balloon is oversized to the vessel. In addition, the low-pressure inflation feature of this variation is suitable for the present invention because the functional requirement of the expandable balloon is merely to engage the ablation element against a circumferential path along the inner lining of the pulmonary vein wall.

Moreover, a circumferential ablation member is adapted to conform to the geometry of the pulmonary vein ostium, at least in part by providing substantial compliance to the expandable member, as was shown and described previously by reference to FIGS. 7A–B. Further to this conformability to pulmonary vein ostium as provided in the specific design of FIGS. 7A–B, the working length L of expandable member (370) is also shown to include a taper which has a distally reducing outer diameter from a proximal end (372) to a distal end (374). In either a compliant or the non-compliant balloon, such a distally reducing tapered geometry adapts the circumferential ablation element to conform to the funneling geometry of the pulmonary veins in the region of their ostia in order to facilitate the formation of a circumferential conduction block there.

Further to the circumferential electrode element embodiment as shown variously throughout the previous illustrative Figures, the circumferential electrode element is coupled to an ablation actuator (190). Ablation actuator (190) generally includes a radio-frequency ("RF") current source (not shown) that is coupled to both the RF electrode element and also a ground patch (195) which is in skin contact with the patient to complete an RF circuit. In addition, ablation actuator (190) preferably includes a monitoring circuit (not shown) and a control circuit (not shown) which together use either the electrical parameters of the RF circuit or tissue parameters such as temperature in a feedback control loop to drive current through the electrode element during ablation. Also, where a plurality of ablation elements or electrodes in one ablation element are used, a switching means may be used to multiplex the RF current source between the various elements or electrodes.

Figure 10A:
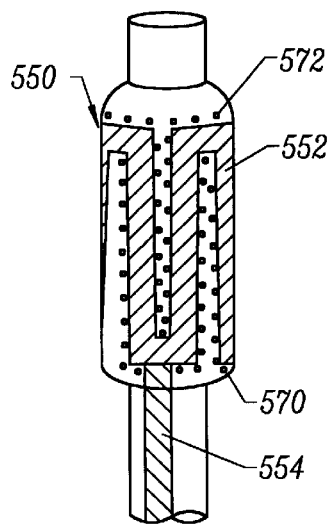
FIGS. 10A–B show perspective views of one circumferential ablation member variation for use in the circumferential ablation device assembly of the present invention, showing a circumferential ablation electrode circumscribing the working length of an expandable member with a secondary shape along the longitudinal axis of the working length which is a modified step shape, the expandable member being shown in a radially collapsed position and also in a radially expanded position, respectively.
Figure 10B:
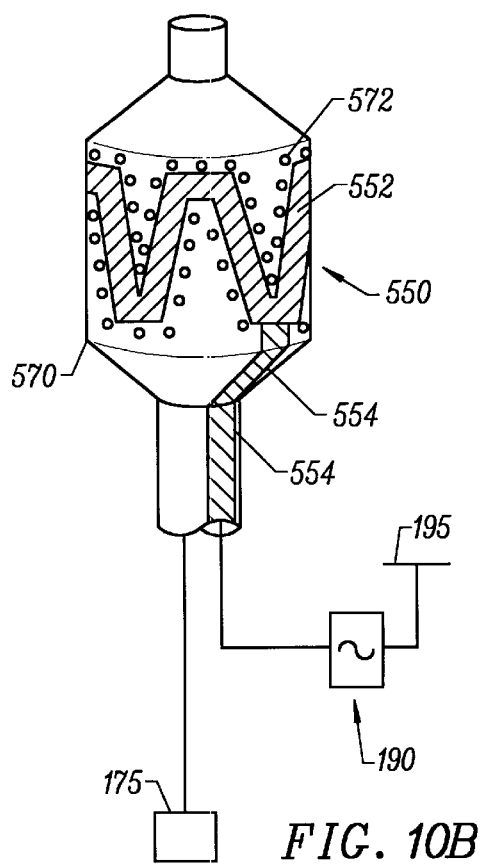

FIGS. 10A–D show various patterns of electrically conductive, circumferential electrode bands as electrode ablation elements, each circumscribing an outer surface of the working length of an expandable member. FIGS. 10A–B show circumferential ablation member (550) to include a continuous circumferential electrode band (552) that circumscribes an outer surface of an expandable member (570). FIG. 10B more specifically shows expandable member (570) as a balloon which is fluidly coupled to a pressurizeable fluid source (175), and further shows electrode band (circumferential ablation element) (552) electrically coupled via electrically conductive lead (554) to ablation actuator (190). In addition, a plurality of apertures (572) are shown in the balloon skin wall of expandable member (570) adjacent to electrode band (552). The purpose of these apertures (572) is to provide a positive flow of fluid such as saline or ringers lactate fluid into the tissue surrounding the electrode band (552). Such fluid flow is believed to reduce the temperature rise in the tissue surrounding the electrode element during RF ablation.

The shapes shown collectively in FIGS. 10A–D allow for a continuous electrode band to circumscribe an expandable member's working length over a range of expanded diameters, a feature which is believed to be particularly useful with a relatively compliant balloon as the expandable member. In the particular embodiments of FIGS. 10A–D, this feature is provided primarily by a secondary shape given to the electrode band relative to the longitudinal axis of the working length of the expandable member. Electrode band (552) is thus shown in FIGS. 10A–B to take the specific secondary shape of a modified step curve. Other shapes than a modified step curve are also suitable, such as the serpentine or sawtooth secondary shapes shown respectively in FIGS. 10C–D. Other shapes in addition to those shown in FIGS. 10A–D and which meet the defined functional requirements are further contemplated within the scope of the present invention.

Figure 10C:
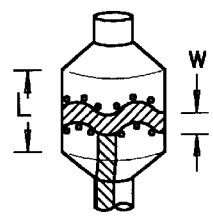
FIGS. 10C–D show perspective views of two circumferential ablation electrodes which form equatorial or otherwise circumferentially placed bands that circumscribe the working length of an expandable member and that have serpentine and sawtooth secondary shapes, respectively, relative to the longitudinal axis of the expandable member when adjusted to a radially expanded position.
Figure 10D:
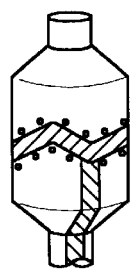

In addition, the electrode band provided by the circumferential ablation elements shown in FIGS. 10C–D and also shown schematically in FIGS. 3–5 has a functional band width w relative to the longitudinal axis of the working length which is only required to be sufficiently wide to form a complete conduction block against conduction along the walls of the pulmonary vein in directions parallel to the longitudinal axis. In contrast, the working length L of the respective expandable element is adapted to securely anchor the distal end portion in place such that the ablation element is firmly positioned at a selected region of the pulmonary vein for ablation. Accordingly, the band width w is relatively narrow compared to the working length L of the expandable element, and the electrode band may thus form a relatively narrow equatorial band which has a band width that is less than two-thirds or even one-half of the working length of the expandable element. Additionally, it is to be noted here and elsewhere throughout the specification, that a narrow band may be placed at locations other than the equator of the expandable element, preferably as long as the band is bordered on both sides by a portion of the working length L.

In another aspect of the narrow equatorial band variation for the circumferential ablation element, the circumferential lesion formed may also be relatively narrow when compared to its own circumference, and may be less than two-thirds or even one-half its own circumference on the expandable element when expanded. In one arrangement which is believed to be suitable for ablating circumferential lesions in the pulmonary veins as conduction blocks, the band width w is less than 1 cm with a circumference on the working length when expanded that is greater than 1.5 cm.

Figure 11A:
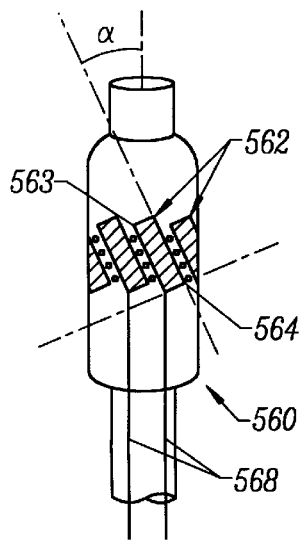
FIGS. 11A–B show perspective views of another circumferential ablation element which includes a plurality of individual ablation electrodes that are spaced circumferentially to form an equatorial band which circumscribes the working length of an expandable member either in an equatorial location or an otherwise circumferential location that is bounded both proximally and distally by the working length, and which are adapted to form a continuous circumferential lesion while the working length is adjusted to a radially expanded position.
Figure 11B:
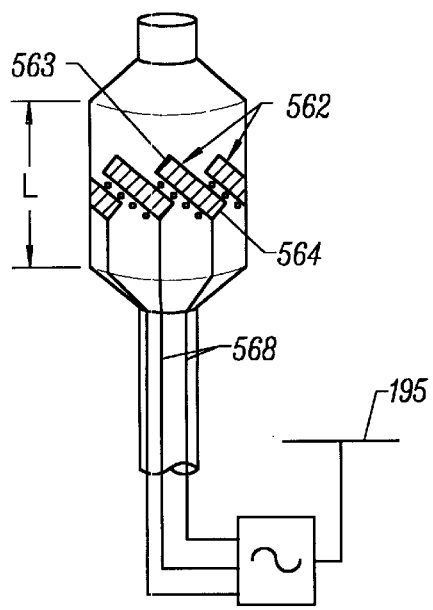

FIGS. 11A–B show a further variation of a circumferential ablation element which is adapted to maintain a continuous circumferential lesion pattern over a range of expanded diameters and which includes electrode elements that form a relatively narrow equatorial band around the working length of an expandable balloon member. In this variation, a plurality of individual electrode/ablation elements (562) are included in the circumferential ablation element and are positioned in spaced arrangement along an equatorial band which circumscribes an outer surface of the expandable member's working length L.

The size and spacing between these individual electrode elements (562), when the balloon is expanded, is adapted to form a substantially continuous circumferential lesion in pulmonary vein wall tissue when in intimal contact adjacent thereto, and is further adapted to form such a lesion over a range of band diameters as the working length is adjusted between a variety of radially expanded positions. Each individual electrode element (562) has two opposite ends (563,564), respectively, along a long axis LA and also has a short axis SA, and is positioned such that the long axis LA is at an acute angle relative to the longitudinal axis La of the elongate catheter body and expandable member (560). At least one of the ends (563,564) along the long axis LA overlaps with an end of another adjacent individual electrode element, such that there is a region of overlap along their circumferential aspect, i.e., there is a region of overlap along the circumferential coordinates. The terms "region of overlap along their circumferential coordinate" are herein intended to mean that the two adjacent ends each are positioned along the working length with a circumferential and also a longitudinal coordinate, wherein they share a common circumferential coordinate. In this arrangement, the circumferential compliance along the working length which accompanies radial expansion of the expandable member also moves the individual electrode elements apart along the circumferential axis. However, the spaced, overlapping arrangement described allows the individual ablation elements to maintain a certain degree of their circumferential overlap, or at least remain close enough together, such that a continuous lesion may be formed without gaps between the elements.

The construction for suitable circumferential electrode elements in the RF variation of the present invention, such as the various electrode embodiments described with reference to FIGS. 10A–12B, may comprise a metallic material deposited on the outer surface of the working length using conventional techniques, such as by plasma depositing, sputter coating, chemical vapor deposition, other known techniques which are equivalent for this purpose, or otherwise affixing a metallic shaped member onto the outer surface of the expandable member such as through known adhesive bonding techniques. Other RF electrode arrangements are also considered within the scope of the present invention, so long as they form a circumferential conduction block as previously described. For example, a balloon skin may itself be metallized, such as by mixing conductive metal, including but not limited to gold, platinum, or silver, with a polymer to form a compounded, conductive matrix as the balloon skin.

Still further to the RF electrode embodiments, another circumferential ablation member variation (not shown) may also include an expandable member, such as an inflatable balloon, that includes a porous skin that is adapted to allow fluid, such as hypertonic saline solution, to pass from an internal chamber defined by the skin and outwardly into surrounding tissues. Such a porous skin may be constructed according to several different methods, such as by forming holes in an otherwise contiguous polymeric material, including mechanically drilling or using laser energy, or the porous skin may simply be an inherently porous membrane. In any case, by electrically coupling the fluid within the porous balloon skin to an RF current source (preferably monopolar), the porous region of the expandable member serves as an RF electrode wherein RF current flows outwardly through the pores via the conductive fluid. In addition, it is further contemplated that a porous outer skin may be provided externally of another, separate expandable member, such as a separate expandable balloon, wherein the conductive fluid is contained in a region between the porous outer skin and the expandable member contained therein. Various other "fluid electrode" designs than those specifically herein described may also be suitable according to one of ordinary skill upon review of this disclosure.

In the alternative, or in addition to the RF electrode variations just described, the circumferential ablation element may also include other ablative energy sources or sinks, and particularly may include a thermal conductor that circumscribes the outer circumference of the working length of an expandable member. Examples of suitable thermal conductor arrangements include a metallic element which may for example be constructed as previously described for the more detailed RF embodiments above. However, in the thermal conductor embodiment such a metallic element would be generally either resistively heated in a closed loop circuit internal to the catheter, or conductively heated by a heat source coupled to the thermal conductor. In the latter case of conductive heating of the thermal conductor with a heat source, the expandable member may be for example a polymeric balloon skin which is inflated with a fluid that is heated either by a resistive coil or by bipolar RF current. In any case, it is believed that a thermal conductor on the outer surface of the expandable member is suitable when it is adapted to heat tissue adjacent thereto to a temperature between 40 deg and 80 deg Celsius.

Further to the thermal conduction variation for the circumferential ablation element, the perfusion balloon embodiment as shown in FIGS. 5A–B may be particularly useful in such a design. It is believed that ablation through increased temperatures, as provided by example above may also enhance coagulation of blood in the pulmonary vein adjacent to the expandable member, which blood would otherwise remain stagnant without such a perfusion feature.

Figure 12:
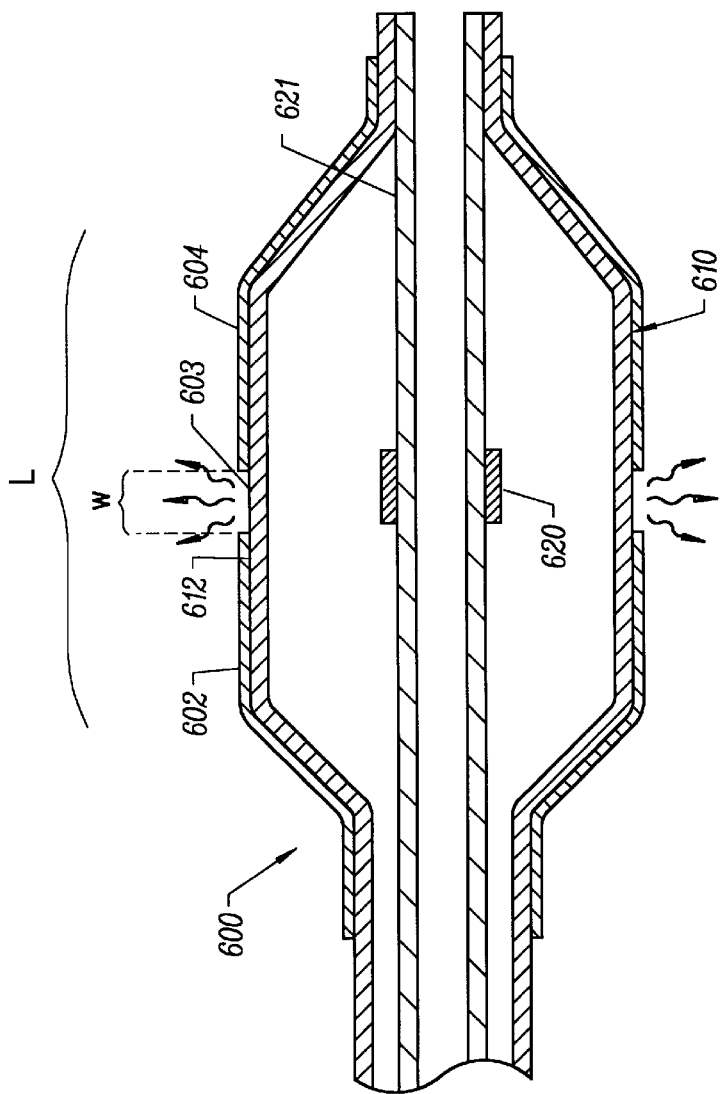
FIG. 12 shows a cross-sectional view of another circumferential ablation member for use in the circumferential ablation device assembly according to the present invention, wherein the circumferential ablation element circumscribes an outer surface of an expandable member substantially along its working length and is insulated at both the proximal and the distal ends of the working length to thereby form an uninsulated equatorial band in a middle region of the working length or otherwise circumferential region of the working length which is bounded both proximally and distally by end portions of the working length, which member is adapted to ablate a circumferential path of tissue in a pulmonary wall adjacent to the equatorial band.

One further circumferential ablation element design which is believed to be highly useful in performing the methods according to the present invention is shown in FIG. 12 to include a circumferential ablation member (600) with two insulators (602,604) that encapsulate the proximal and distal ends, respectively, of the working length L of an expandable member (610). In the particular embodiment shown, the insulators (602,604) are thermal insulators, such as a thermal insulator comprising a Teflon material. Expandable member (610) is an inflatable balloon which has a balloon skin (612) that is thermally conductive to surrounding tissue when inflated with a heated fluid which may contain a radiopaque agent, saline fluid, ringers lactate, combinations thereof, other known biocompatible fluids having acceptable heat transfer properties for these purposes, further to the thermal conductor embodiments previously described. By providing these spaced insulators, a circumferential ablation element is formed as an equatorial band (603) of uninsulated balloon skin is located between the opposite insulators. In this configuration, the circumferential ablation element is able to conduct heat externally of the balloon skin much more efficiently at the uninsulated equatorial band (603) than at the insulated portions, and thereby is adapted to ablate only a circumferential region of tissue in a pulmonary vein wall which is adjacent to the equatorial band. It is further noted that this embodiment is not limited to an "equatorial" placement of the ablation element. Rather, a circumferential band may be formed anywhere along the working length of the expandable member and circumscribing the longitudinal axis of the expandable member as previously described.

FIG. 12 further shows use of a radiopaque marker (620) to identify the location of the equatorial band (603) in order to facilitate placement of that band at a selected ablation region of a pulmonary vein via X-ray visualization. Radiopaque marker (620) is opaque under X-ray, and may be constructed for example of a radiopaque metal such as gold, platinum, or tungsten, or may comprise a radiopaque polymer such as a metal loaded polymer. FIG. 12 shows radiopaque marker (620) positioned coaxially over an inner tubular member (621) which is included in a coaxial catheter design as would be apparent to one of ordinary skill. The present invention contemplates the combination of such a radiopaque marker additionally in the other embodiments herein shown and described. To note, when the circumferential ablation member which forms an equatorial band includes a metallic electrode element, such electrode may itself be radiopaque and may not require use of a separate marker as just described.

The thermal insulator embodiment just described by reference to FIG. 12 is illustrative of a broader embodiment, wherein a circumferential ablation member has an ablating surface along the entire working length of an expandable member, but is shielded from releasing ablative energy into surrounding tissues except for along an unshielded or uninsulated equatorial band. As such, the insulator embodiment contemplates other ablation elements, such as the RF embodiments previously described above, which are provided along the entire working length of an expandable member and which are insulated at their ends to selectively ablate tissue only about an uninsulated equatorial band.

In a further example using the insulator embodiment in combination with a circumferential RF electrode embodiment, a metallized balloon which includes a conductive balloon skin may have an electrical insulator, such as a polymeric coating, at each end of the working length and thereby selectively ablate tissue with electricity flowing through the uninsulated equatorial band. In this and other insulator embodiments, it is further contemplated that the insulators described may be only partial and still provide the equatorial band result. For instance, in the conductive RF electrode balloon case, a partial electrical insulator will allow a substantial component of current to flow through the uninsulated portion due to a "shorting" response to the lower resistance in that region.

In still a further example of an insulator combined with an RF ablation electrode, a porous membrane comprises the entire balloon skin of an expandable member. By insulating the proximal and distal end portions of the working length of the expandable member, only the pores in the unexposed equatorial band region are allowed to effuse the electrolyte which carries an ablative RF current.

Further to the expandable member design for use in a circumferential ablation element according to the present invention, other expandable members than a balloon are also considered suitable. For example, in one expandable cage embodiment shown in FIG. 13, cage (650) comprises coordinating wires (651) and is expandable to engage a desired ablation region in a pulmonary vein.

The radial expansion of cage (650) is accomplished as follows. Sheath (652) is secured around the wires proximally of cage (650). However, core (653), which may be a metallic mandrel such as stainless steel, extends through sheath (652) and distally within cage (650) wherein it terminates in a distal tip (656). Wires (651) are secured to distal tip (656), for example by soldering, welding, adhesive bonding, heat shrinking a polymeric member over the wires, or any combination of these methods. Core (653) is slideable within sheath (652), and may for example be housed within a tubular lumen (not shown) within sheath (652), the wires being housed between a coaxial space between the tubular lumen and sheath (652). By moving the sheath (652) relative to core (653) and distal tip (656)(shown by arrows in FIG. 13), the cage (650) is collapsible along its longitudinal axis in order to force an outward radial bias (also shown with arrows in FIG. 13) to wires (651) in an organized fashion to formed a working length of cage (650) which is expanded (not shown).

Figure 13:
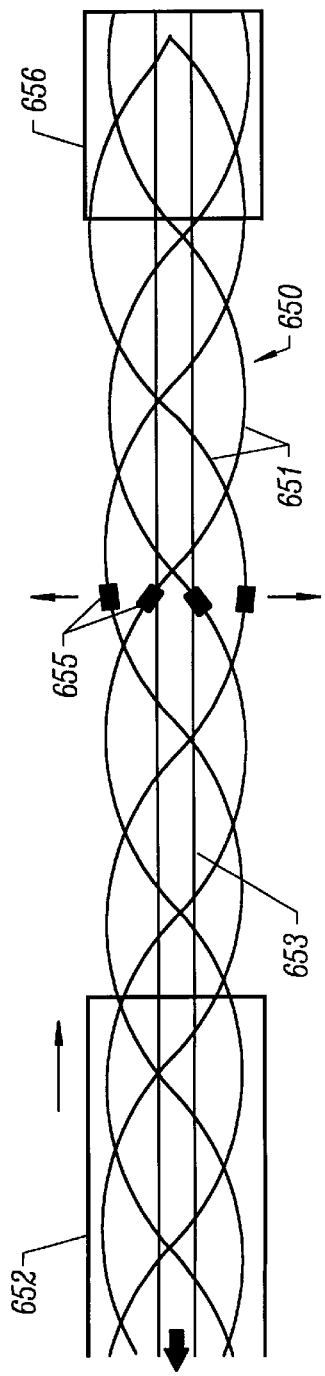
FIG. 13 shows a perspective view of another circumferential ablation member which is adapted for use in the circumferential ablation device assembly of the present invention, wherein the expandable member is shown to be a cage of coordinating wires which are adapted to be adjusted from a radially collapsed position to a radially expanded position in order to engage electrode elements on the wires about a circumferential pattern of tissue in a pulmonary vein wall.

Further to the particular expandable cage embodiment shown in FIG. 13, a plurality of ablation electrodes (655) is shown, each being positioned on one of wires (651) and being similarly located along the longitudinal axis of the cage (650). The radial bias given to wires (651) during expansion, together with the location of the ablation electrodes (655), serves to position the plurality of ablation electrodes/elements (655) along a circumferential, equatorial band along the expanded working length of cage (650). The wires forming a cage according to this embodiment may also have another predetermined shape when in the radially expanded position. For example, a taper similar to that shown for expandable member (370) in FIGS. 7A–B may be formed by expanding cage (650), wherein the ablation element formed by ablation electrodes (655) may be positioned between the proximal end and the distal end of the taper.

Further to the construction of the embodiment shown in FIG. 13, wires (651) are preferably metal, and may comprise stainless steel or a superelastic metal alloy, such as an alloy of nickel and titanium, or a combination of both. Regarding the case of nickel and titanium construction for wires (655), a separate electrical conductor may be required in order to actuate ablation electrodes (655) to efficiently emit ablative current into surrounding tissues. In the case where wires (651) are constructed of stainless steel, they may also serve as electrical conductors for ablation electrodes (655). Further to the stainless steel design, the wires (651) may be coated with an electrical insulator to isolate the electrical flow into surrounding tissues at the site of the ablation electrodes (655). Moreover, the ablation electrodes (655) in the stainless steel wire variation may be formed simply by removing electrical insulation in an isolated region to allow for current to flow into tissue only from that exposed region.

In a further cage embodiment (not shown) to that shown in FIG. 13, a circumferential strip of electrodes may also be secured to the cage (650) such that the strip circumscribes the cage at a predetermined location along the cage's longitudinal axis. By expanding cage (650) as previously described, the strip of electrodes are adapted to take a circumferential shape according to the shape of the expanded cage (650). Such an electrode strip is preferably flexible, such that it may be easily reconfigured when the cage is adjusted between the radially collapsed and expanded positions and such that the strip may be easily advanced and withdrawn with the cage within the delivery sheath. Furthermore, the electrode strip may be a continuous circumferential electrode such as a conductive spring coil, or may be a flexible strip which includes several separate electrodes along its circumferential length. In the latter case, the flexible strip may electrically couple all of the electrodes to a conductive lead that interfaces with a drive circuit, or each electrode may be separately coupled to one or more such conductive leads.

Figure 14:
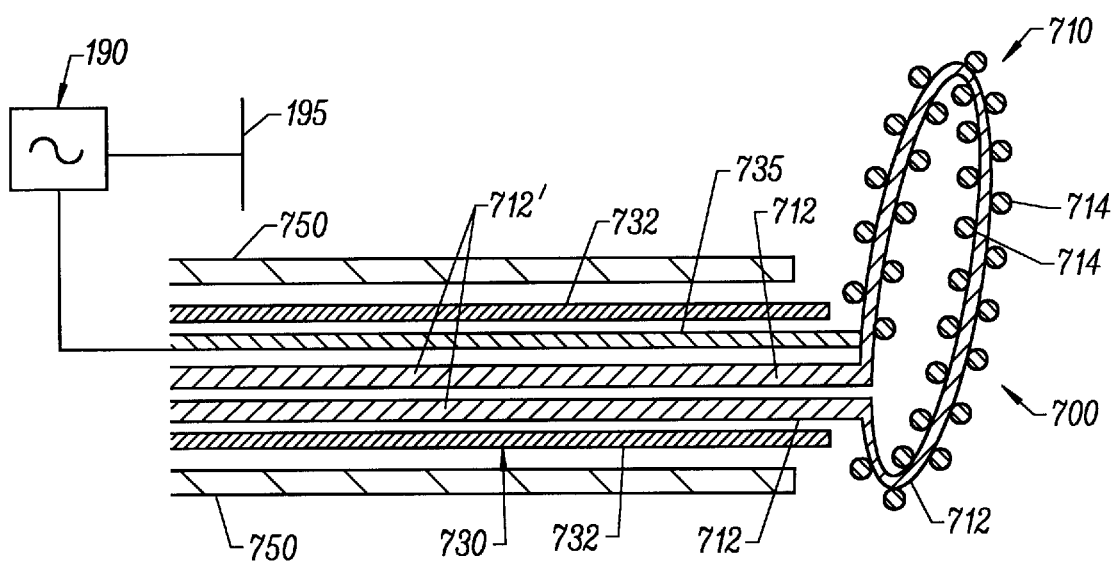
FIG. 14 shows a cross-sectional view of another circumferential ablation element which is adapted for use in the circumferential ablation device assembly of the present invention. A superelastic, looped electrode element is shown at the distal end of a pusher and is adapted to circumferentially engage pulmonary vein wall tissue to form a circumferential lesion as a conduction block that circumscribes the pulmonary vein lumen.

Another circumferential ablation element adapted for use in the circumferential conduction block assembly according to the present invention is shown in FIG. 14, wherein circumferential ablation member (700) includes a looped member (710) attached, preferably by heat shrinking, to a distal end of a pusher (730). Looped member (710) and pusher (730) are slideably engaged within delivery sheath (750) such that looped member (710) is in a first collapsed position when positioned and radially confined within delivery sheath (750), and expands to a second expanded position when advanced distally from delivery sheath (750).

Looped member (710) is shown in more detail in FIG. 14 to include a core (712) which is constructed of a superelastic metal alloy such as a nickel-titanium alloy and which has a looped portion with shape memory in the looped configuration. This looped configuration is shown in FIG. 14 to be in a plane which is off-axis, preferably perpendicular, to the longitudinal axis of the pusher (730). This off-axis orientation of the loop is adapted to engage a circumferential path of tissue along a pulmonary vein wall which circumscribes the pulmonary vein lumen when the looped member (710) is delivered from the delivery sheath (750) when the delivery sheath is positioned within the vein lumen parallel to its longitudinal axis. An ablation electrode (714) is also shown in FIG. 14 as a metallic coil which is wrapped around core (712) in its looped portion.

Pusher (730) is further shown in FIG. 14 to include a tubular pusher member (732) which is heat shrunk over two ends (712') of core (712) which extend proximally of looped member (710) through pusher (730) in the particular variation shown. While in this embodiment core (712) extends through the pusher in order to provide stiffness to the composite design for the pusher, it is further contemplated that the superelastic metal of the core may be replaced or augmented in the pusher region with another different mandrel or pusher core (not shown), such as a stiffer stainless steel mandrel. Also shown within pusher (730) is an electrically conductive lead (735) which is coupled to the ablation electrode (714) and which is also adapted in a proximal region of the pusher (not shown) to couple to an ablation actuator (190) such as an RF current source (shown schematically).

While particular detailed description has been herein provided for particular embodiments and variations according to the present invention, it is further understood that various modifications and improvements may be made by one of ordinary skill according to this disclosure and without departing from the broad scope of the invention.

What is claimed is:

1. A tissue ablation device system that ablates a circumferential region of tissue at a location where a pulmonary vein extends from a posterior left atrial wall of a left atrium in a patient, comprising:

an elongate body with a proximal end portion, a distal end portion and a longitudinal axis;

an inflatable balloon located along the distal end portion and having a working length along the longitudinal axis which is adjustable between a radially collapsed position and a radially expanded position, the working length further being defined between first and second ends and having a first end portion, a second end portion, an intermediate portion positioned between the first and second end portions, and an expanded outer diameter when in the radially expanded position which is sufficient along the intermediate portion to engage the circumferential region of tissue, and a circumferential ablation element having a circumferential band that is located along the distal end portion at a position relative to the longitudinal axis that generally coincides with the intermediate portion and that is substantially spaced from the first and second ends such that movement of the elongated body moves the inflatable balloon and the circumferential band together, the circumferential band also having a band width along the longitudinal axis which is shorter than the working length and being adapted to ablatively couple to a circumferential area surrounding only the intermediate portion such that tissue ablation principally occurs along the circumferential region of tissue when engaged by the intermediate portion and spaced from the first and second ends of the working length in the radially expanded position.

2. The system of claim 1, wherein the circumferential band further comprises an ablation electrode which is electrically coupled to a conductive lead and which is adapted to emit current into the circumferential region of tissue engaged by the intermediate portion in the radially expanded position when the conductive lead is also coupled to an ablation actuator which includes an electrical current source.

3. The system of claim 2, further comprising:

a return electrode adapted to be secured to and in electrical contact with the patient's body and which is coupled to a ground lead;

an ablation actuator which includes a radio-frequency current source which is adapted to couple to both the ground lead and also to a conductive lead connected to the ablation electrode; and wherein a radio-frequency ablation circuit is formed upon actuation and includes the ablation actuator, the conductive lead, the ablation electrode, the patient's body, the return electrode, and the ground lead.

4. The system of claim 1, wherein the working length of the inflatable balloon when adjusted to the radially expanded position is adapted to engage a pulmonary vein ostium of the pulmonary vein.

5. The system of claim 4, wherein the working length of the inflatable balloon further comprises a proximal region and a distal region and has a shape when in the radially expanded position that includes a taper with a distally reducing outer diameter from the proximal region to the distal region.

6. The system of claim 5, wherein the intermediate portion overlaps at least in part with the proximal region and the circumferential band is located along the taper in the proximal region.

7. The system of claim 1, wherein the working length of the inflatable balloon is adjustable between a plurality of radially expanded positions having a range of expanded outer diameters at least along the intermediate portion; and the circumferential band is adapted to ablatively couple to the circumferential area and to ablate a continuous circumferential lesion pattern in tissue engaged by the intermediate region over the range of expanded outer diameters.

8. The system of claim 7, wherein the circumferential band further comprises a circumference and a secondary shape which defines an overall band length relative to the longitudinal axis such that the overall band length shortens as the circumference of the circumferential band increases when the working length is expanded between two of the plurality of radially expanded positions.

9. The system of claim 8, wherein the secondary shape is selected from the group of shapes consisting of a serpentine shape and a sawtooth shape.

10. The system of claim 7, wherein the circumferential band comprises a plurality of individual ablation element portions positioned in a circumferentially spaced arrangement about the longitudinal axis, each of said individual ablation element portions comprising a long axis and a short axis, the long axis having two opposite end portions, each of said individual ablation element portions also being positioned with its long axis skewed at an angle relative to the longitudinal axis, and each end portion of each of said individual ablation element portions being positioned to form a circumferential overlap region with another end portion of another adjacent individual ablation element portion; and whereby adjusting the working length between two radially expanded positions, the position of each individual ablation element portion is adjusted relative to each adjacent individual ablation element portion such that the circumferential overlap regions between adjacent individual ablation element portions are reduced although maintained.

11. The system of claim 7, wherein the inflatable balloon when adjusted to each of the radially expanded positions is adapted to engage each of a plurality of pulmonary vein ostia having different inner diameters.

12. The system of claim 11, wherein the inflatable balloon comprises a substantially compliant balloon material which is adapted to engage each of the plurality of pulmonary vein ostia when the inflatable balloon is expanded to a corresponding radially expanded position in a left atrium and advanced retrogradedly from the left atrium against the respective ostium.

13. The system of claim 12, wherein the substantially compliant balloon material is selected from the group of materials consisting of silicone, latex rubber, and polyvinyl chloride.

14. The system of claim 1, wherein the band width is less than two-thirds of the working length.

15. The system of claim 1, wherein the radially expanded position of the intermediate portion has a circumference, and the band width is less than two-thirds of the circumference.

16. The system of claim 1, further comprising:

a linear ablation member located at least in part along the distal end portion and which has an elongate ablation element length and a linear ablation element, said linear ablation member being adapted to form a continuous linear lesion in tissue adjacent to the linear ablation element when the linear ablation element is coupled to an ablation actuator.

17. The system of claim 16, wherein the linear ablation element further comprises an electrode which is coupled to an electrical conductor which has a proximal conductor end in the region of the proximal end portion that is adapted to couple to an electrical current source.

18. The system of claim 16, wherein the linear ablation element further comprises a plurality of spaced electrodes, each electrode being coupled to an electrical conductor which has a proximal conductor end in the region of the proximal end portion that is adapted to couple to an electrical current source.

19. The system of claim 16, wherein the linear ablation member further comprises first and second linear ablation member ends, the first linear ablation member end being located adjacent to the expandable member which forms at least in part a first anchor adapted to secure the first linear ablation member end near a pulmonary vein ostium of the pulmonary vein along the posterior left atrial wall; and a second anchor is coupled to the second linear ablation member end and is adapted to secure the second linear ablation member end to a second location along the posterior left atrial wall.

20. The system of claim 19, wherein each of the first and second anchors further comprises a guidewire tracking member which forms a bore having first and second guidewire ports and which is adapted to track over a guidewire which is slideably received into the bore through the first and second guidewire ports.

21. The system of claim 1, wherein a circumferential portion of the working length that is located along the intermediate portion is adapted to be energized by an energy source and thereby forms at least in part the circumferential band.

22. The system of claim 21, wherein the working length in the radially expanded position defines at least in part an interior chamber; and the circumferential ablation element further comprises an interior energy source located within the interior chamber, said interior energy source being adapted to couple energy to and thereby energize the circumferential portion.

23. The system of claim 1, wherein the working length further comprises an outer surface along the intermediate region; and the circumferential band further comprises at least a portion of an exterior energy source that circumscribes the outer surface of the working length.

24. The system of claim 23, wherein the exterior energy source comprises at least a portion of an ablation electrode assembly which is adapted to couple to an electrical current source.

25. The system of claim 24, wherein the ablation electrode assembly includes first and second electrode end portions with an intermediate electrode portion extending therebetween along the longitudinal axis; and an electrical insulator is disposed on an outer surface of each of the first and second electrode end portions, such that only the intermediate electrode portion is substantially uninsulated and electrically exposed to thereby form the circumferential band.

26. The system of claim 24, wherein the circumferential band has a shape with an overall length that extends along the intermediate portion and between the first and second end portions.

27. The system of claim 1, wherein the circumferential band is adapted to emit a circumferential pattern of energy that ablatively couples to the circumferential area surrounding the intermediate portion.

28. A tissue ablation device system for ablating multiple circumferential regions of tissue with different inner diameters and which are each located where a pulmonary vein extends from a posterior left atrial wall of a left atrium in a patient, comprising:
- an elongate body with a proximal end portion and a distal end portion and a longitudinal axis;
- an expandable member located along the distal end portion and having a working length along the longitudinal axis which is adjustable between a radially collapsed position and a plurality of radially expanded positions which correspond to a range of outer diameters wherein the working length is adapted to engage each of the multiple circumferential regions of tissue; and
- a circumferential ablation element which is coupled to the distal end portion in a fixed position relative to the working length and is adapted in each of the radially expanded positions to ablatively couple to a circumferential area surrounding the working length and to ablate a substantially continuous, transmural circumferential pattern in each of the multiple circumferential regions of tissue, respectively, when engaged by the working length.

29. The system of claim 28, wherein the circumferential ablation element further comprises a circumferential band which circumscribes the working length with a circumference, a band width relative to the longitudinal axis, and a secondary shape relative to the longitudinal axis that defines an overall band length relative to the longitudinal axis, and the secondary shape is adapted such that the overall band length shortens as the circumference increases when the working length is expanded to between multiple ones of the plurality of radially expanded positions.

30. The system of claim 29, wherein the secondary shape is selected from the group of shapes consisting of a serpentine shape and a sawtooth shape.

31. The system of claim 28, wherein the circumferential ablation element further comprises a circumferential band having a plurality of individual ablation elements positioned along the working length in a circumferentially spaced pattern about the longitudinal axis, each said individual ablation element comprising a long axis and a short axis, the long axis having two opposite end portions, each said individual ablation element also being positioned with its long axis skewed at an angle relative to the longitudinal axis, and each end portion of each said individual ablation element being positioned to form a circumferential overlap region with another end portion of another adjacent individual ablation element; and
- whereby adjusting the working length between two of the radially expanded positions, the position of each individual ablation element is adjusted relative to each adjacent individual ablation element such that the circumferential overlap regions between adjacent individual ablation elements are reduced although maintained.

32. The system of claim 28, wherein the expandable member when adjusted to each of the radially expanded positions is adapted to engage each of a variety of pulmonary vein ostia having different inner diameters.

33. The system of claim 32, wherein the working length has a proximal region, a distal region, and a shape in at least one of the radially expanded positions which comprises a taper with a distally reducing outer diameter from the proximal region to the distal region.

34. The system of claim 33, wherein the circumferential area surrounds the taper along the proximal region.

35. The system of claim 32, further comprising:
- a linear ablation member which is located at least in part along the distal end portion and which has an elongate ablation element length and a linear ablation element, and which is adapted to form a continuous linear lesion in tissue adjacent to the linear ablation element when the linear ablation element is coupled to and actuated by an ablation actuator.

36. The system of claim 35, wherein the linear ablation element further comprises an electrode which is coupled to an electrical conductor which has a proximal conductor end in the region of the proximal end portion that is adapted to couple to an electrical current source.

37. The system of claim 35, wherein the linear ablation element further comprises a plurality of spaced electrodes, each electrode being coupled to an electrical conductor which has a proximal conductor end in the region of the proximal end portion that is adapted to couple to an ablation actuator which is an electrical current source.

38. The system of claim 28, further comprising:
- a linear ablation member which is located at least in part along the distal end portion and which has an elongate ablation element length and a linear ablation element, and which is adapted to form a continuous linear lesion in tissue adjacent to the linear ablation element when the linear ablation element is coupled to and actuated by an ablation actuator.

39. The system of claim 38, wherein the linear ablation element further comprises an electrode which is coupled to an electrical conductor which has a proximal conductor end in the region of the proximal end portion that is adapted to couple to an electrical current source.

40. The system of claim 38, wherein the linear ablation element further comprises a plurality of spaced electrodes, each electrode being coupled to an electrical conductor which has a proximal conductor end in the region of the proximal end portion that is adapted to couple to an ablation actuator which is an electrical current source.

41. The system of claim 38, wherein the linear ablation member further comprises first and second linear ablation member ends, the first linear ablation member end being located adjacent to the expandable member which forms at least in part a first anchor adapted to secure the first linear ablation member end near a pulmonary vein ostium of the pulmonary vein along the posterior left atrial wall; and
- a second anchor is coupled to the second linear ablation member end and is adapted to secure the second linear ablation member end to a second location along the posterior left atrial wall.

42. The system of claim 41, wherein each of the first and second anchors further comprises a guidewire tracking member which forms a bore having first and second guidewire ports and which is adapted track over a guidewire which is slideably received into the bore through the first and second guidewire ports.

43. The system of claim 28, wherein the expandable member comprises an inflatable balloon which is constructed of a substantially compliant material.

44. The system of claim 43, wherein the substantially compliant material is selected from the group of materials consisting of silicone, latex rubber, and polyvinyl chloride.

45. A tissue ablation device system that ablates a circumferential region of tissue at a location where a pulmonary vein extends from a posterior left atrial wall of a left atrium in a patient, comprising:

an elongate body with a proximal end portion and a distal end portion and a longitudinal axis;

an expandable member located along the distal end portion and having a working length with a longitudinal dimension defined between ends of the working length along the longitudinal axis and which is adjustable between a radially collapsed position and a radially expanded position with an expanded outer diameter that is larger than a radially collapsed diameter, the working length also being positionable within the pulmonary vein and being adapted to engage the circumferential region of tissue when in the radially expanded position; and a circumferential ablation element which is coupled to the working length of the expandable member such that movement of the elongated body moves the expandable member and the circumferential ablation element together, the circumferential ablation element being substantially spaced from the ends of the working length and being adapted to ablate the circumferential region of tissue when the working length is engaged to the circumferential region of tissue in the radially expanded position and also when the ablation element is actuated.

46. The system of claim 45, wherein the working length of the expandable member has a shape when in the radially expanded position that includes a taper with a distally reducing outer diameter from a proximal region to a distal region.

47. The system of claim 45, further comprising:

a linear ablation member that is located at least in part along the distal end portion and which has an elongate ablation element length and a linear ablation element which is adapted to form a continuous linear lesion in tissue adjacent to the linear ablation element when the linear ablation element is coupled to and actuated by an ablation actuator.

48. The system of claim 47, wherein the linear ablation element further comprises an electrode which is coupled to an electrical conductor which has a proximal conductor end in the region of the proximal end portion that is adapted to couple to an electrical current source.

49. The system of claim 47, wherein the linear ablation element further comprises a plurality of spaced electrodes, each electrode being coupled to an electrical conductor which has a proximal conductor end in the region of the proximal end portion that is adapted to couple to an electrical current source.

50. The system of claim 45, wherein the diameter of the working length in the radially expanded position is larger than the longitudinal dimension of the working length.

51. A tissue ablation device system that ablates a circumferential region of tissue at a location where a pulmonary vein extends from a posterior left atrial wall of a left atrium in a patient, comprising:

an elongated body with a proximal end portion and a distal end portion and a longitudinal axis;

an expandable member located along the distal end portion and having a working length along the longitudinal axis which is adjustable between a radially collapsed position and a radially expanded position which has an outer diameter which is larger when in the radially expanded position than when in the radially collapsed position, the working length also being adapted to engage the pulmonary vein ostium when in the radially expanded position;

a circumferential ablation element which is coupled to the working length of the expandable member, which is adapted to couple to and ablate the circumferential region of tissue when the expandable member is engaged to the circumferential region of tissue in the radially expanded position;

a linear ablation member coupled to the distal end portion of the elongate member with first and second linear ablation element ends and a linear ablation element therebetween which is adapted to ablate a continuous linear lesion in tissue adjacent thereto when the linear ablation element is coupled to and actuated by an ablation actuator, the first linear ablation member end being coupled to the expandable member which forms at least in part a first anchor adapted to secure the first linear ablation member end within the pulmonary vein ostium; and a second anchor coupled to the second linear ablation member end which is adapted to secure the second linear ablation member end to a second location along the left atrium wall.

52. A tissue ablation device system for ablating a circumferential region of tissue at a location where a pulmonary vein extends from a posterior left atrial wall of a left atrium in a patient, comprising:

an elongated body with a proximal end portion, a distal end portion and a longitudinal axis;

an expandable member located along the distal end portion with a working length along the longitudinal axis which is adjustable between a radially collapsed position and a radially expanded position, the working length having a first portion, a second portion, and an intermediate portion between the first and second portions along the longitudinal axis, and the working length at least along the intermediate portion being further constructed to define an interior space when in the radially expanded position; and a circumferential ablation element having a circumferential band which is comprised of a porous membrane and which circumscribes the interior space at a location along the intermediate portion of the working length of the expandable member, the circumferential band in the radially expanded position having a band width along the longitudinal axis which is shorter than the working length and also having an expanded outer diameter which is adapted to engage the circumferential region of tissue, the porous membrane having an inner surface which is adapted to fluidly couple to a pressurizeable source of electrically conductive fluid, and the porous membrane further being adapted to pass a volume of electrically conductive fluid from the inner surface, externally through the porous membrane, and into the circumferential region of tissue when engaged by the circumferential band in the radially expanded position, the circumferential ablation element further including an ablation electrode which is adapted to electrically couple to an electrical current source and also to the volume of electrically conductive fluid which passes through the porous membrane.

53. The system of claim 52, wherein the porous membrane is disposed substantially along the working length and includes first and second membrane end portions with a middle membrane portion extending therebetween along the longitudinal axis; and an insulator is located along each of the first and second membrane end portions and is adapted to block the passage of conductive fluid from the inner surface and through the porous membrane into surrounding tissue, such that only the middle membrane portion is uninsulated and is adapted to pass electrically conductive fluids from the inner surface and into tissue adjacent to the middle membrane portion, the middle membrane portion thereby forming at least in part the circumferential band.

54. The system of claim 52, further comprising:

a pressurizeable conductive fluid source which includes a fluid reservoir that contains an electrically conductive fluid, the pressurizeable conductive fluid source being adapted to fluidly couple to the inner surface and thereby force the electrically conductive fluid through the porous membrane and into the circumferential region of tissue;

a return electrode adapted to be secured to and in electrical contact with the patient's body and which is coupled to a ground lead; and an ablation actuator which is a radio-frequency current source and which is adapted to electrically couple to both the conductive fluid passing through the porous membrane and also to the ground lead;

wherein a radio-frequency ablation circuit is formed upon actuation of the ablation actuator, the radio-frequency ablation circuit including the radiofrequency current source, a volume of electrically conductive fluid flowing through the porous membrane into the circumferential region of tissue, the patient's body, the return electrode, and the ground lead.

55. The system of claim 52, wherein the expandable member further comprises an outer surface along the working length; and the porous membrane is disposed around and circumscribes the working length such that a pressurizeable electrolyte fluid chamber is formed at least in part between the inner surface of the porous membrane and the outer surface of the expandable member, wherein the pressurizeable electrolytic fluid chamber is adapted to couple to a pressurizeable source of electrically conductive fluid.

56. A tissue ablation device system that ablates a circumferential region of tissue at a location where a pulmonary vein extends from a posterior left atrial wall of a left atrium in a patient, comprising:

an elongated body with a proximal end portion, a distal end portion and a longitudinal axis;

an expandable member located along the distal end portion with a working length along the longitudinal axis which is adjustable between a radially collapsed position and a radially expanded position; and a circumferential ablation element having a circumferential band that is comprised of a thermal conductor and that is located along the distal end portion at a position relative to the longitudinal axis that generally coincides with the working length of the expandable member, the circumferential band further having a band width along the longitudinal axis which is shorter than the working length, wherein the radially expanded position the working length at least at the location coinciding with the circumferential band has an outer diameter that is sufficient to engage the circumferential region of tissue, and wherein the circumferential band is adapted to emit a circumferential pattern of thermal energy into the circumferential region of tissue when the circumferential region of tissue is engaged by the working length in the radially expanded position and when the thermal conductor is coupled to and actuated by a thermal ablation actuator.

57. The system of claim 56, wherein the thermal conductor is positioned substantially along the working length of the expandable member and includes first and second conductor end portions with an intermediate conductor portion extending therebetween along the longitudinal axis; and a thermal insulator is disposed on each of the first and second conductor end portions, such that the intermediate conductor portion is substantially uninsulated and thermally exposed to thereby form the circumferential band.

58. The system of claim 56, wherein the thermal conductor further comprises an electrical conductor which is adapted to resistively heat and emit thermal energy when coupled to and actuated by an electrical current source.

59. The system of claim 56, wherein the thermal conductor is adapted to be conductively heated and thereby emit thermal energy when coupled to and actuated by a thermal energy source.

60. The system of claim 59, wherein the expandable member further comprises an inflatable balloon which forms a balloon chamber that is coupled to a fluid passageway which extends along the longitudinal axis of the elongate body and terminates in a proximal inflation port in the region of the proximal end portion of the elongate body, the proximal inflation port being adapted to couple to a pressurizeable fluid source; and the circumferential ablation element further comprises a heater element adapted to heat fluid within the balloon chamber, wherein the heated fluid in the balloon chamber heats the thermal conductor which in turn emits heat into the circumferential region of tissue engaged by the working length in the radially expanded position.

61. The system of claim 56, wherein a circumferential portion of the working length is thermally conductive and forms at least in part the circumferential band.

62. The system of claim 61, wherein the working length in the radially expanded position defines at least in part an interior space; and the circumferential ablation element further comprises an interior thermal energy source located within the interior space and which is adapted to couple thermal energy to and thereby heat the circumferential portion.

63. The system of claim 56, wherein the working length of the expandable member further comprises an outer surface; and the circumferential band comprises an exterior thermal conductor that circumscribes the outer surface of the working length.

64. A tissue ablation device system that ablates a circumferential region of tissue at a location where a pulmonary vein extends from a posterior left atrial wall of a left atrium in a patient, comprising:

an elongated body with a proximal end portion and a distal end portion and a longitudinal axis;

an inflatable balloon located along the distal end portion which is coupled to a fluid passageway that extends between the inflatable balloon and a proximal inflation port that is adapted to couple to a pressurizeable fluid source, the inflatable balloon also being comprised of a substantially compliant balloon material and having a working length along the longitudinal axis which is adjustable between a radially collapsed position and a radially expanded position which has an expanded outer diameter that is sufficient to engage the circumferential region of tissue; and an ablation element coupled to the elongate body and adapted to couple to an ablation actuator, and also when actuated, to ablatively couple to a circumferential area surrounding the working length, whereby adjusting the inflatable balloon to the radially expanded position in the left atrium and thereafter forcing the inflatable balloon retrogradedly against the pulmonary vein ostium, the working length is adapted to engage a pulmonary vein ostium of the pulmonary vein along the posterior left atrial wall such that the circumferential area is positioned along the circumferential region of tissue and wherein the ablation element is adapted to couple to and ablate the circumferential region of tissue.

65. The system of claim 64, wherein the substantially compliant balloon material is selected from the group of materials consisting of silicone, latex rubber, and polyvinyl chloride.

66. The system of claim 64, wherein:

the circumferential ablation element is coupled to a circumferential band that circumscribes the working length of the inflatable balloon in the radially expanded position, the circumferential band having a band width along the longitudinal axis which is shorter than the working length, and the circumferential ablation element being adapted to ablate the circumferential region of tissue when the circumferential band is engaged to the circumferential region of tissue and the circumferential ablation element is coupled to and actuated by an ablation actuator.

67. The system of claim 64, wherein:

the working length is adjustable to a plurality of radially expanded positions which correspond to a range of expanded outer diameters along the working length, the range of expanded outer diameters being larger than a collapsed outer diameter of the inflatable balloon when in the radially collapsed position; and whereby adjusting the inflatable balloon to multiple ones of the plurality of radially expanded positions within the left atrium and thereafter advancing the inflatable balloon retrogradedly against the pulmonary vein ostium, the inflatable balloon is adapted to engage each of a plurality of such circumferential regions of tissue having different inner diameters.

68. The system of claim 51, wherein each of the first and second anchors further comprises a guidewire tracking member which forms a bore having first and second guidewire ports and which is adapted track over a guidewire which is slideably received into the bore through the first and second guidewire ports.

69. The system of claim 51, wherein the expandable member is adjustable to a plurality of radially expanded positions which correspond to a range of expanded outer diameters along the working length, wherein each radially expanded position the expandable member is adapted to engage a different circumferential region of tissue having a different inner diameter.

70. A tissue ablation device assembly that ablates a circumferential region of tissue at a location where a pulmonary vein extends from a posterior left atrial wall of a left atrium in a patient, comprising:

an elongate body with a proximal end portion, a distal end portion and a longitudinal axis; and a circumferential ablation member with an inflatable balloon located along the distal end portion and having a working length along the longitudinal axis which is adjustable between a radially collapsed position and a radially expanded position, the working length having an expanded outer diameter in the radially expanded position that is larger than when in the radially collapsed position and that is sufficient to engage the circumferential region of tissue, and a circumferential ablation element having a single circumferential band also located along the distal end portion at a position relative to the longitudinal axis generally coinciding with the working length of the inflatable balloon such that movement of the elongate body moves the inflatable balloon and the circumferential ablation element together, the circumferential band being adapted to couple to and be actuated by an ablation actuator such that the circumferential ablation element ablatively couples to only a circumferential area that surrounds the circumferential bond wherein the circumferential ablation element is adapted to ablate only the circumferential region of tissue in a circumferential pattern when the working length is engaged to the circumferential region of tissue in the radially expanded position.

71. The system of claim 70, wherein a circumferential portion of the working length is adapted to be energized by an energy source to thereby form at least in part the circumferential band.

72. The system of claim 71, wherein the circumferential portion comprises a porous membrane.

73. The system of claim 71, wherein the working length in the radially expanded position defines at least in part an interior chamber; and the circumferential ablation element further comprises an interior energy source located within the interior chamber and which is adapted to couple energy to and thereby energize the circumferential portion.

74. The system of claim 70, wherein the working length further comprises an outer surface; and the circumferential band further comprises an exterior energy source that circumscribes the outer surface of the working length.

75. The system of claim 1, 28, 45, 56, 64, 51, or 70, wherein the ablation element further comprises an electrode ablation element.

76. The system of claim 1, 28, 45, 56, 64, 51, or 70, wherein the ablation element further comprises a microwave ablation element.

77. The system of claim 1, 28, 45, 56, 64, 51, or 70, wherein the ablation element further comprises a cryogenic ablation element.

78. The system of claim 1, 28, 45, 56, 64, 51, or 70, wherein the ablation element further comprises an ultrasonic ablation element.

79. The system of claim 1, 28, 45, 56, 64, 51, or 70, wherein the ablation element further comprises a light emitting element ablation element.

80. The system of claim 1, 28, 45, 56, 64, 51, or 70, wherein the ablation element further comprises a thermal conduction ablation ablation element.

81. The system of claim 1, 28, 45, 56, 64, 51, or 70, wherein the ablation element further comprises a porous membrane.

* * * * *

UNITED STATES PATENT AND TRADEMARK OFFICE
CERTIFICATE OF CORRECTION

PATENT NO. : 6,024,740
DATED : February 15, 2000
INVENTOR(S) : Lesh, et al.

It is certified that error appears in the above-identified patent and that said Letters Patent is hereby corrected as shown below:

Column 36,
Line 21, change "bond wherein" to -- band, wherein --.
Line 62, change "ablation ablation element" to -- ablation element --.

Signed and Sealed this

Twenty-sixth Day of February, 2002

Attest:

JAMES E. ROGAN
Attesting Officer     Director of the United States Patent and Trademark Office